United States Patent [19]

Lee-Huang et al.

[11] Patent Number: 5,317,009
[45] Date of Patent: May 31, 1994

[54] ANTI-HIV PROTEINS GAP 31, DAP 30 AND DAP 32 AND THERAPEUTIC USES THEREOF

[75] Inventors: Sylvia Lee-Huang, New York, N.Y.; Hsiang-fu Kung, Middletown, Md.; Paul L. Huang; Philip L. Huang, both of Boston, Mass.; Peter Huang; Henry I. Huang, both of New York, N.Y.; Hao-chia Chen, Potomac, Md.

[73] Assignees: New York University, New York, N.Y.; American Biosciences, Inc., Boston, Mass.; National Institutes of Health, Bethesda, Md.

[21] Appl. No.: 749,541

[22] Filed: Aug. 26, 1991

[51] Int. Cl.$^5$ .................. C07K 13/00; C07K 15/10; C07K 15/14
[52] U.S. Cl. .......................... 514/8; 514/12; 514/885; 530/370; 530/377; 530/387.1; 530/395
[58] Field of Search ............ 530/370, 377, 387.1, 530/395; 514/8, 12, 885; 424/195.1

[56] References Cited

U.S. PATENT DOCUMENTS 4,795,739 1/1989 Litson et al. .................. 514/8

OTHER PUBLICATIONS

Ho, et al (1991) Biochimica Biophysica Acta 1088: 311–314.
Goodman in *Basic and Clinical Immunology*, 5th ed. (Stites, et al., eds.) Lange Medical Publications, Los Altos, Calif., 1984, pp. 21-22.
Lee-Huang, et al (1991) FEBS Letters 291 (1): 139–144.
Montecucchi, et al (1989) Int. J. Peptide Protein Res 33: 263–267.
Goldmacher, et al (Oct. 1989) Journal of Cellular Physiology 141 (1): 222–234.
Sivam, et al (Jun. 15, 1987) Cancer Research 47: 3169–3173.

*Primary Examiner*—Che S. Chereskin
*Attorney, Agent, or Firm*—Browdy and Neimark

[57] ABSTRACT

New proteins, termed GAP 31, obtainable from the seeds of *Gelonium multiflorum*, and DAP 30 and DAP 32, obtainable from the leaves or seeds of *Dianthus caryophyllus*, or the above proteins produced by recombinant means, are useful for treating HIV infections. In treating HIV infections, the protein is administered alone or in conjunction with other anti-HIV therapeutics. Also provided are processes for purifying the proteins, DNA sequences encoding the proteins, hosts expressing the proteins, recombinant DNA methods for expressing the proteins, and antibodies specific for the proteins.

3 Claims, 5 Drawing Sheets

ANTI-HIV PROTEINS GAP 31, DAP 30 AND DAP 32 AND THERAPEUTIC USES THEREOF

FIELD OF THE INVENTION

The present invention in the fields of virology and oncology relates to GAP 31, an anti-HIV protein purified from Gelonium plant extracts, and DAP 30 and DAP 32 anti-HIV proteins purified from Dianthus extracts, DNA encoding these proteins, antibodies specific for these proteins, and uses of these proteins in treating HIV infection.

BACKGROUND OF THE INVENTION

HIV Infection and AIDS

Human Immunodeficiency Virus (HIV), the etiological agent for AIDS (Acquired Immune Deficiency Syndrome), is a member of the lentiviruses, a subfamily of retroviruses. Many retroviruses are well-known carcinogens. HIV per se is not known to cause cancer in humans or other animals, but it does present a formidable challenge to the host. HIV integrates its genetic information into the genome of the host. The viral genome contains many regulatory elements which allow the virus to control its rate of replication in both resting and dividing cells. Most importantly, HIV infects and invades cells of the immune system; it destroys the body's immune system and renders the patient susceptible to opportunistic infections and neoplasms. The immune defect appears to be progressive and irreversible, with a high mortality rate that approaches 100% over several years.

HIV is transmitted by parenteral inoculation and/or intimate sexual contact. It is estimated that about 2 million people in the United States are currently infected with HIV, and 5 to 10 million people are infected worldwide. Recent projections indicate that a majority of those now infected will develop AIDS within a seven year follow-up period. In 1989 alone, over 130,000 cases of AIDS were reported domestically, and more than half of these patients have died. An additional 100,000 cases were diagnosed in the United States by the end of 1990. Reports to the World Health Organization suggested that at least a million new cases of AIDS can be expected within the next five years worldwide. It is apparent that AIDS is an unprecedented threat to global health. The search for effective therapies to treat AIDS is of paramount importance.

HIV-1 is trophic and cytopathic for T4 lymphocytes, cells of the immune system which express the cell surface differentiation antigen CD4 (also known as OKT4, T4 and leu3). The viral tropism is due to the interactions between the viral envelope glycoprotein, gp120, and the cell-surface CD4 molecules (Dalgleish, A. G. et al., *Nature* 312:763-767 (1984)). These interactions not only mediate the infection of susceptible cells by HIV but are also responsible for the virus-induced fusion of infected and uninfected T cells. This cell fusion results in the formation of giant multinucleated syncytia, cell death, and progressive depletion of CD4 cells in AIDS patients. These events result in HIV-induced immunosuppression and its subsequent sequelae, opportunistic infections and neoplasms.

In addition to CD4+ T cells, the host range of HIV includes cells of the mononuclear phagocytic lineage (Dalgleish, A. G. et al., supra), including blood monocytes, tissue macrophages, Langerhans cells of the skin and dendritic reticulum cells within lymph nodes. HIV is also neurotropic, capable of infecting monocytes and macrophages in the central nervous system causing severe neurologic damage. Macrophage/monocytes are a major reservoir of HIV. They may interact and fuse with CD4-bearing T cells, causing T cell depletion and thus contributing to the pathogenesis of AIDS.

Anti-HIV Drugs

Intensive efforts are currently under way to develop therapies to prevent or intervene in the development of clinical symptoms in HIV-infected individuals. For the most part, efforts have been focused on the use of nucleoside analogue drugs such as AZT (azidothymidine), and on other dideoxynucleoside derivatives such as ddA, ddT, ddI, and ddC. These drugs inhibit the viral enzyme, reverse transcriptase, thereby inhibiting de novo infection of cells. However, once viral infection has been established within a cell, viral replication utilizes host cell enzymes. Thus, drugs which inhibit only reverse transcriptase would be expected to have limited effects. While the spread of free virus within the organism may be blocked, the mechanisms of syncytium formation and pathogenesis through direct intercellular spread remain.

A very small number of HIV-infected T cells can fuse with, and eventually kill, large numbers of uninfected T cells through mechanisms based on viral surface antigen expression. In vitro studies have demonstrated HIV replication even in the continued presence of nucleoside analogues in prolonged culture. Drugs targeting other viral processes are also being developed, such as soluble CD4 and dextran sulfate to inhibit viral binding, alpha interferons and "ampligen" to inhibit viral budding, and castanospermine to inhibit the processing of the viral glycoproteins. These drugs are still in early stages of testing. The actual processes of HIV intracellular replication and protein synthesis have not been specifically targeted because these viral functions were thought to reflect the mere pirating of normal host processes through host mechanisms.

Immunotoxins and Their Limitations

Immunotoxins, have been developed by conjugating a protein toxin to a monoclonal antibody via a linker for targeted therapy, in particular, of tumors (Vitetta, E. S. et al., *Ann. Rev. Immunol.* 3:197-212 (1985)). In principle, an injected immunotoxin is transported through the blood stream to the targeted tissue, penetrates the tissue, binds to the individual cells expressing the antigen to which the antibody is directed. The toxin bound to the antibody then acts in a highly localized manner to destroy only the cells to which the antibody is bound. All three components of the conjugates are important for the specific achievement of cytotoxicity: the antibody enables specific retention in the target tissue by binding to a specific cell-surface antigen, which enhances cellular uptake by the target cells. The linker keeps the toxin bound to the antibody and inactive while in circulation, but allows for rapid release of the active toxin inside the target cells. The toxin kills the cell by inhibiting cellular protein synthesis, or by some other related mechanism.

Some of the most cytotoxic substances known are protein toxins of bacterial and plant origin (Frankel, A. E. et al., *Ann. Rev. Med.* 37:125-142 (1986)). The cytotoxic action of these molecules involves two events—binding the cell surface and inhibition of cellular protein synthesis. The most commonly used plant toxins are ricin and abrin; the most commonly used bacterial toxins are diphtheria toxin and Pseudomonas exotoxin A.

In ricin and abrin, the binding and toxic functions are contained in two separate protein subunits, the A and B chains. The ricin B chain binds to the cell surface carbohydrates and promotes the uptake of the A chain into the cell. Once inside the cell, the ricin A chain inhibits protein synthesis by inactivating the 60S subunit of the eukaryotic ribosome Endo, Y. et al., *J. Biol. Chem.* 262: 5908–5912 (1987)).

Diphtheria toxin and Pseudomonas exotoxin A are single chain proteins, and their binding and toxicity functions reside in different domains of the same protein chain. In diphtheria toxin, the C-terminal domain inhibits protein synthesis by ADP-ribosylation of the elongation factor, EF2. The two activities are separate, and the toxin elicits its full activity only after proteolytic cleavage between the two domains. Pseudomonas exotoxin A has the same catalytic activity as diphtheria toxin.

The use of diphtheria toxin-based immunotoxins is limited by the fact that most people have been immunized against diphtheria toxin. The use of ricin-based immunotoxins is also limited because these immunotoxins exhibit specific toxicity only in the presence of lactose, which at high concentrations competes with the cell surface carbohydrates for the B chain binding sites. An alternative approach has been developed to use ricin A chain or "single chain ribosome inactivating protein" (SCRIP) in the preparation of immunotoxins.

Single Chain Ribosome Inactivating Proteins (SCRIPs) and Their Potential Application in Antiviral or Tumor Therapy Trichosanthin (Gu, Z. et al., *Acta Chemica Sinica* 43:943–945 (1984)) and the TAP 29 protein derived therefrom (Lee-Huang, S. et al. *Proc. Natl. Acad. Sci. USA*, 88:6570–6574 (1991)), as well as the novel proteins of the present invention, belong to the family of single chain ribosome-inactivating proteins (SCRIPs). SCRIPs are highly active at inactivating ribosomes in cell-free systems, but are relatively nontoxic to intact cells. Also known as "type 1 ribosome-inactivating proteins," SCRIPs catalytically inhibit in vitro eukaryotic protein synthesis Stripe, F. et al., *FEBS Lett.* 195:1–8 (1986)) by specific cleavage of the N-glycosidic linkage of adenosine at residue A4324 of eukaryotic 28S ribosomal RNA (rRNA) (Endo, Y. et al., *J. Biol. Chem.* 262:8128–8130 (1987)). This impairs the interaction of the elongation factor EF2 with the 60S ribosomal subunit, thus abrogating polypeptide chain elongation. SCRIPs are basic proteins with a pI in the range of pH 8 to 10, and molecular weights generally in the range of about 24 to 33 kDa.

A wide variety of SCRIPs are found in plants, including trichosanthin and TAP 29, Momordica-derived inhibitors (Barbieri, L. et al., *Biochem. J.* 186:443–452 (1980); Jimenez, A. et al., *Annu. Rev. Microbiol.* 39:649–672 (1985)), and the pokeweed anti-viral proteins (PAP) (Irvin, J. D., *Arch. Biochem. Biophys.* 169:522–528 (1975); Irvin, J. D. et al., *Arch. Biochem. Biophys.* 200:418–425 (1980); Barbieri, L. et al., *Biochem. J.* 203:55–59 (1982)). MAP 30, a protein recently isolated in the laboratory of the present inventors from *Momordica charantia*, has potent anti-HIV activity with little cytotoxicity (Lee-Huang, S. et al., *FEBS Lett.* 272:12–18 (1990)), In addition dianthins (Stripe, F. et al., *Biochem. J.* 195:399–405 (1981)) and gelonin (Stripe, F. et al., *J. Biol. Chem.* 255:6947–53 (1980)) are known SCRIPs. The amino acid and sugar compositions of gelonin and the dianthins have been reported previously (Falasca, A. et al., *Biochem. J.* 207:505–09 (1982)). No amino acid sequence of these proteins has been reported.

Many of these SCRIPs, or conjugates thereof, have varying degrees of selective anti-viral or anti-tumor activity, but are commonly associated with nonspecific cytotoxicity (McGrath, M. S. et al., *Proc. Natl. Acad. Sci. USA* 86:2844–2848 (1989); Zarling, J. M. et al., *Nature* 347:92–95 (1990)).

M. S. McGrath et al. (supra) reported that GLQ 223, a SCRIP isolated from *T. kirilowii*, selectively inhibits HIV replication. Treatment of cells with GLQ 223 resulted in selective inhibition of the synthesis of viral DNA, RNA, and protein, with less effect on cellular synthesis. The mechanisms of the selective anti-HIV activity of GLQ 223 is not known. It has not been established whether this activity is associated with the ribosome-inactivating or the abortifacient activity of this compound.

Lifson et al., U.S. Pat. No. 4,795,739, disclosed that plant proteins, including trichosanthin, reduced viral antigen expression in, and were selectively toxic to, HIV-infected cells. These proteins were said to be useful for treating HIV infections in humans.

The cytotoxic side effects of trichosanthin are well known (Qian, R. Q. et al., *Acta Chemica Sinica* 39:927–931 (1981); Gu, Z. et al. *Acta Chemica Sinica* 43:943–945 (1984)) since it has been used for centuries in Chinese traditional medicine, in particular for abortion and treatment of trophoblastic tumors (Li, S. C. (1596) Pen Ts'ao Kang Mu, (Chinese Pharmaceutical Compendium) reprinted by People's Medical Publishing House, Beijing (1977); Cheng, K. F., *Obstet. Gynecol.* 59:494–498 (1982); Chan, W. Y. et al., *Contraception* 29:91–100 (1984)). The cytotoxicity of GLQ 223 has also been documented in recent clinical trials in the United States (Palcca, J., *Science* 247:1406 (1990)). Thus, concerns with therapeutic safety of a number of these plant derived agents represent serious obstacles in their utility as anti-HIV therapeutics.

SUMMARY OF THE INVENTION

The present inventors' laboratories recently reported the purification and characterization of two new anti-HIV proteins, MAP 30 and TAP 29 (Lee-Huang et al., 1990, 1991 supra) which share amino acid sequence homology with the ribosome-inactivating proteins, trichosanthin and ricin A chain (Gu, Z. et al., supra; Zhang, X. et al., supra).

The present inventors conceived that SCRIPs from distinct and unrelated plant species might have similar effects on human immunodeficiency virus type 1 (HIV-1). The present inventors discovered, and determined the N-terminal amino acid sequence of, a new class of anti-HIV SCRIPs from the seeds of *Gelonium multiflorum* (*Euphorbiaceae himalaya*) and the leaves of *Dianthus caryophyllus* (carnation). The proteins of the present invention possess high antiviral potency but low toxicity to normal cells in culture as well as to intact animals.

It is an object of the present invention to overcome the aforementioned deficiencies of the prior work, in particular the toxicity of plant-derived SCRIPs to normal cells which is a severe impediment to their clinical utility (e.g., Palcca, J., supra).

The present invention provides an anti-HIV protein, GAP 31, obtainable from the seeds of *Gelonium multiflorum*, or a functional derivative thereof.

The present invention provides an anti-HIV protein obtainable from the seeds of the plant *Gelonium multiflorum* (*Euphorbiaceae himalaya*) substantially free of other proteins or glycoproteins, or a functional derivative thereof, the protein or functional derivative preferably having anti-HIV activity in vitro at concentrations of about 0.3 nanomolar and preferably lacking non-specific cytotoxicity in vitro at concentrations of about 300 nanomolar.

In a preferred embodiment, the above protein is GAP 31, having a molecular weight of about 31 kD as determined by SDS polyacrylamide gel electrophoresis and having an N-terminal amino acid sequence SEQ ID No:1 (see, also, Table 1).

It is not possible to compare the GAP 31 protein of the present invention to gelonin because the amino acid sequence of gelonin has not been reported.

The present invention also provides an anti-HIV protein obtainable from the leaves or seeds of the plant *Dianthus caryophyllus* substantially free of other proteins or glycoproteins, or a functional derivative thereof, the protein or functional derivative preferably having anti-HIV activity in vitro at concentrations of about 0.76 nanomolar and preferably lacking non-specific cytotoxicity in vitro at concentrations of about 30–300 nanomolar.

In one embodiment, the protein obtainable from Dianthus is DAP 30, having a molecular weight of about 30 kD as determined by SDS polyacrylamide gel electrophoresis and having an N-terminal amino acid sequence SEQ ID No:2 (see Table 1).

In another embodiment, the protein obtainable from Dianthus is DAP 32, having a molecular weight of about 32 kD as determined by SDS polyacrylamide gel electrophoresis and having an N-terminal amino acid sequence SEQ ID No:3 (see Table 1).

Since the amino acid sequences of the dianthins have not been reported, it is impossible to compare their sequences with DAP 30 and DAP 32 of the present invention.

The proteins of the present invention may be purified from plant material. Alternatively, the proteins or functional derivatives may be produced by recombinant DNA techniques or chemical synthesis, or a combination thereof.

TABLE 1

N-terminal Amino Acid Sequences of GAP 31, DAP 30 and DAP 32 and Their Comparison with Other SCRIPs

| | 1 | | | | | | | | | 10 | | | | | | | | | | 20 | | | | | | | | | | 30 |
|---|---|---|---|---|---|---|---|---|---|---|---|---|---|---|---|---|---|---|---|---|---|---|---|---|---|---|---|---|---|---|
| DAP 30 | | A | T | A | Y | T | L | N | L | A | N | P | S | A | S | Q | Y | S | X | F | L | D | Q | I | R | N | N | V | R | D |
| DAP 32 | A | V | K | T | I | T | L | N | L | V | S | P | S | A | N | R | Y | A | T | F | L | T | E | I | R | D | N | V | R | X |
| GAP 31 | G | L | D | T | V | S | F | S | T | K | G | A | T | Y | I | T | Y | V | N | F | L | N | E | L | R | V | K | T | K | P |
| MAP 30 | | | | D | V | N | F | D | L | S | T | A | T | A | K | T | Y | T | K | F | I | E | D | F | R | A | T | L | P | F |
| TAP 29 | | | | D | V | S | F | R | L | S | G | A | T | S | K | K | K | V | Y | F | I | S | N | L | R | K | A | L | P | N |
| TRI 1 | | | | D | V | S | F | R | L | S | G | A | T | S | S | S | Y | G | V | F | I | S | N | L | R | K | A | L | P | N |
| RIC A | | | | I | I | N | F | T | T | A | G | A | T | V | Q | S | Y | T | N | F | I | R | A | V | R | G | R | L | T | T |
| | 24 | | | | | | | | | | | | | | | | | | | | | | | | | | | | | 53 |
| SAP 6 | A | V | T | S | L | T | L | D | L | V | N | P | T | A | G | Q | Y | S | S | F | V | D | K | F | V | D | K | I | R | N |
| | 31 | | | | | | | | | 40 | | | | | | | | | | 50 | | | | | | | | | | 60 |
| DAP 30 | T | S | L | I | Y | G | G | T | D | V | A | V | I | G | A | P | S | T | T | D | K | F | L | R | L | N | F | Q | G | P |
| DAP 32 | R | S | L | D | Y | S | H | S | G | I | D | V | I | G | A | P | S | S | R | D | S | X | L | N | I | N | F | Q | S | P |
| GAP 31 | E | G | N | S | H | G | I | P | S | L | R | K | S | S | D | D | P | G | S | S | F | V | V | A | G | | | | | |
| MAP 30 | S | H | K | V | Y | D | I | P | L | I | R | S | S | I | S | A | P | | | | | | | | | | | | | |
| TAP 29 | E | K | K | L | Y | D | L | P | L | V | R | S | S | X | S | G | S | | | | | | | | | | | | | |
| TRI 1 | E | R | K | L | Y | D | I | P | L | I | R | S | S | L | P | G | S | | | | | | | | | | | | | |
| RIC A | G | A | D | V | R | H | E | I | P | V | R | L | P | L | P | I | N | | | | | | | | | | | | | |
| | 54 | | | | | | | | | | | | | | | | | | | | | | | | | | | | | 83 |
| SAP 6 | P | N | L | K | Y | G | G | T | D | I | A | V | I | G | X | P | P | S | K | E | K | F | L | R | I | N | F | Q | S | S |

Ricin A chain (Ric A) residues are from 7 to 51. SAP-6 sequence is for residues 24–83. Sequences were aligned to maximize similarities between the proteins.

The present invention also provides a process for purifying a protein having anti-HIV activity from the seeds of the plant *Gelonium multiflorum* comprising: (a) extracting the leaves with 10 mM sodium phosphate buffer, pH 7.2, containing 0.15 M NaCl (PBS); (b) centrifuging the extract at least once, and recovering the supernatant; (c) ammonium sulfate precipitation of the supernatant; and (d) purifying the ammonium sulfate precipitate by ion-exchange chromatography and Con A sepharose affinity chromatography, and recovering the protein, thereby purifying the protein.

The present invention also provides a process for purifying a protein having anti-HIV activity from the leaves or seeds (or both) of the plant *Dianthus caryophyllus*, comprising: (a) extracting the leaves with 10 mM sodium phosphate buffer, pH 7.2, containing 0.15 M NaCl (PBS); (b) centrifuging the extract at least once, and recovering the supernatant; (c) ammonium sulfate precipitation of the supernatant; and (d) purifying the ammonium sulfate precipitate by ion-exchange chromatography and Con A sepharose affinity chromatography, and recovering the protein, thereby purifying the protein.

The present invention is directed to a DNA sequence encoding GAP 31 or a functional derivative thereof, substantially free of other DNA sequences.

The present invention is also directed to a DNA sequence encoding DAP 30 or a functional derivative thereof, substantially free of other DNA sequences.

The present invention is further directed to a DNA sequence encoding DAP 32 or a functional derivative thereof, substantially free of other DNA sequences.

The DNA may be genomic DNA, or preferably, cDNA. The DNA sequence preferably comprises an expressible vehicle.

The invention also provides prokaryotic and eukaryotic host cells, including yeast, mammalian and plant cells, transformed or transfected with the above DNA.

Also provided is a substantially pure protein encoded by the above DNA molecules, expressed in a prokaryotic or eukaryotic host.

Also provided is an antibody specific for GAP 31, DAP 30 or DAP 32 protein, either polyclonal, monoclonal, or chimeric.

The present invention also provides improved methods for treating a subject with an HIV-1 infection. More specifically, the invention is directed to a method for treating a subject infected with HIV-1 comprising administering to the subject an effective amount the GAP 31, DAP 30 or DAP 32 protein or a functional derivative thereof.

The invention is also directed to a method for treating a subject infected with HIV-1 by administering the GAP 31, DAP 30 or DAP 32 protein in combination with any one or more of the known anti-AIDS therapeutics, including, but not limited to, AZT, ddI, ddC, ddA, soluble CD4, TAP 29 and MAP 30, trichosanthin or GLQ 223.

The treatment methods of the invention also include administering to a subject infected with HIV-1 a conjugate of GAP 31, DAP 30 or DAP 32 with soluble CD4, CD4 derivatives, antibodies specific for CD4, or HIV-coded glycoproteins such as gp120 and gp41.

DETAILED DESCRIPTION OF THE PREFERRED EMBODIMENTS

Figure 1:
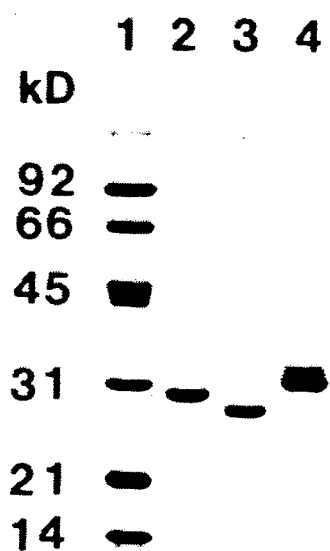
FIG. 1 is a gel pattern of GAP 31, DAP 30 and DAP 32 in SDS-PAGE. Electrophoresis was carried out in the presence of the reducing agent 2-mercaptoethanol in 10% acrylamide at a constant voltage of 90 V for 5 hr, until the bromophenol blue tracking dye reached 1 cm from the lower edge of the gel. The gels were stained with silver stain. Lane 1, molecular weight standards (2 $\mu$g each), lanes 2, 3 and 4, GAP 31 (2 $\mu$g), DAP 30 (2 $\mu$g) and DAP 32 (3 $\mu$g).

The plant proteins of the present invention, GAP 31, DAP 30 and DAP 32 belong to the family of single chain ribosome-inactivating proteins, or SCRIPs.

The seeds of Gelonium multiflorum (Euphorbiaceae himalaya) is the source material for the isolation of the GAP 31 protein. DAP 30 and DAP 32 were purified from leaves of Dianthus caryophyllus (carnation). The source materials for these preparations were supplied by American BioSciences, New York, N.Y.

By the term "anti-HIV activity" is intended the ability to inhibit viral attachment to cells, viral entry into cells, and cellular metabolism which permits viral replication, production and release. Also intended is the inhibition of intercellular spread of the virus. The term is meant to encompass inhibition of synthesis and cellular expression of viral antigens, activity of virus-coded enzymes such as reverse transcriptase and protease, and all known HIV pathogenic actions, such as, for example, immunosuppression. Thus, any activity which tends to inhibit any of these mechanisms is "anti-HIV activity."

GAP 31, DAP 30 or DAP32 are used for treatment of HIV infection either alone, or in combination with other modes of therapy known in the art. Such modes of therapy include chemotherapy with drugs, such as AZT, ddC, ddA, ddT ddI, plant proteins such as MAP 30, or TAP 29, in combination with each other, or with a biologically based therapeutic, such as, for example, soluble CD4, antibodies to CD4, and conjugates of CD4 or anti-CD4.

Because the proteins of the present invention are nontoxic to normal cells, their utility is not limited to the treatment of established HIV infection. For example, the proteins or functional derivatives thereof may be used in the treatment of blood products, such as those maintained in blood banks. The nation's blood supply is currently tested for antibodies to HIV. However, the test is still imperfect and samples which yield negative tests may still contain virus. Thought the risk of developing AIDS from transfusions is currently very low, it is not zero. Treating blood and blood products with the proteins and derivatives of the present invention may add an extra margin of safety, to kill any virus that may have gone undetected. Because of their lack of toxicity, these compounds could even be used to treat condoms, vaginal gels, toothpastes, mouthwashes, or detergents and soaps to minimize the transmission of HIV.

By the term "anti-tumor activity" is intended the ability to inhibit the growth of tumor cells in vitro or in vivo, to inhibit the development of a tumor in vivo from a tumor cell which has undergone tumorigenic transformation in vivo in the subject animal or from a tumor cell which has been implanted in the animal. This term is intended to encompass the actual oncogenic transformation of a cell to become tumorigenic, as well as the ability of a tumor cell to metastasize to or invade an alternate site in the body.

Whenever the term "protein" or "peptide" is used in the present specification or claims, the term is intended to include not only the native protein or peptide but a recombinant protein or peptide having the same amino acid sequence, or a "functional derivative" of the native or recombinant protein or peptide.

By "functional derivative" is meant a "fragment," "variant," "analog," or "chemical derivative" of the protein or peptide of the present invention, which terms are defined below. A functional derivative retains at least a portion of the function of the GAP 31, DAP 30 or DAP 32 protein which permits a utility in accordance with the present invention, such as anti-HIV activity, anti-tumor activity, or immunoreactivity with an antibody specific for GAP 31, DAP 30 or DAP 32.

A "fragment" of GAP 31, DAP 30 or DAP 32 refers to any subset of the molecule, that is, a shorter peptide.

A "variant" of GAP 31, DAP 30 or DAP 32 refers to a molecule substantially similar to either the entire peptide or a fragment thereof. Variant peptides may be conveniently prepared by direct chemical synthesis of the variant peptide, using methods well-known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see European Patent Publication No. EP 75,444).

At the genetic level, these variants ordinarily are prepared by site-directed mutagenesis (as exemplified by Adelman et al., DNA 2:183 (1983)) of nucleotides in the DNA encoding the peptide molecule, thereby producing DNA encoding the variant, and thereafter expressing the DNA in recombinant cell culture. The variants typically exhibit the same qualitative biological activity as the nonvariant peptide.

A preferred group of variants are those in which at least one amino acid residue in a peptide molecule, and preferably, only one, has been removed and a different residue inserted in its place. For a detailed description of protein chemistry and structure, see Schulz, G. E. et al., *Principles of Protein Structure,* Springer-Verlag, New York, 1978, and Creighton, T. E., Proteins: *Structure and Molecular Properties,* W. H. Freeman & Co., San Francisco, 1983, which are hereby incorporated by reference. The types of substitutions which may be made in the protein or peptide molecules of the present invention may be based on analysis of the frequencies of amino acid changes between a homologous protein of different species, such as those presented in Tables 1-2 of Schulz et al. (supra) and FIGS. 3-9 of Creighton (supra). Base on such an analysis, conservative substitutions are defined herein as exchanges within one of the following five groups:

1. Small aliphatic, nonpolar or slightly polar residues: ala, ser, thr (pro, gly);
2. Polar, negatively charged residues and their amides: asp, asn, glu, gln;
3. Polar, positively charged residues: his, arg, lys;
4. Large aliphatic, nonpolar residues: met, leu, ile, val (cys); and
5. Large aromatic residues: phe, tyr, trp.

The three amino acid residues in parentheses above have special roles in protein architecture. Gly is the only residue lacking any side chain and thus imparts flexibility to the chain. Pro, because of its unusual geometry, tightly constrains the chain. Cys can participate in disulfide bond formation which is important in protein folding. Note the Schulz et al. would merge Groups 1 and 2, above. Note also that Tyr, because of its hydrogen bonding potential, has some kinship with Ser, Thr, etc.

Substantial changes in functional or immunological properties are made by selecting substitutions that are less conservative, such as between, rather than within, the above five groups, which will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (a) substitution of gly and/or pro by another amino acid or deletion or insertion of gly or pro; (b) substitution of a hydrophilic residue, e.g., ser or thr, for (or by) a hydrophobic residue, e.g., leu, ile, phe, val or ala; (c) substitution of a cys residue for (or by) any other residue; (d) substitution of a residue having an electropositive side chain, e.g., lys, arg or his, for (or by) a residue having an electronegative charge, e.g., glu or asp; or (e) substitution of a residue having a bulky side chain, e.g., phe, for (or by) a residue not having such a side chain, e.g., gly.

Most deletions and insertions, and substitutions according to the present invention are those which do not produce radical changes in the characteristics of the protein or peptide molecule. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the peptide molecule-encoding nucleic acid, expression of the variant nucleic acid in recombinant cell culture, and, optionally, purification from the cell culture, for example, by immunoaffinity chromatography using a specific antibody on a column (to absorb the variant by binding to at least one epitope).

An "analog" of GAP 31, DAP 30 or DAP 32 refers to a non-natural molecule substantially similar to either the entire molecule or a fragment thereof.

A "chemical derivative" of GAP 31, DAP 30 or DAP 32 contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo- beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'-N-C-N-R') such as 1-cyclohexyl-3-(2-morpholinyl-(4-ethyl) carbodiimide or 1-ethyl-3-(4-azonia-4,4-dimethyl-pentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking GAP 31, DAP 30 or DAP 32, or their functional derivatives to a water-insoluble support matrix or to other macromolecular carriers. Commonly used cross-linking agents include, e.g., 1,1-bis(-diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(-succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (T. E. Creighton, *Proteins: Structure and Molecule Properties*, W. H. Freeman & Co., San Francisco, pp. 79-86 (1983)), acetylation of he N-terminal amine, and, in some instances, amidation of the C-terminal carboxyl groups.

The activity of the cell lysate or purified protein or peptide variant can be screened in a suitable screening assay for the desired characteristic. For example, a change in the immunological character of the protein peptide molecule, such as binding to a given antibody, is measured by a competitive type immunoassay (see below). Biological activity, in particular anti-HIV activity coupled with lack of non-specific cytotoxicity, is screened in an appropriate bioassay, as described in the Examples, below.

Modifications of such peptide properties as redox or thermal stability, hydrophobicity, susceptibility to proteolytic degradation or the tendency to aggregate with carriers or into multimers are assayed by methods well known to the ordinarily skilled artisan.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences*, 16th ed., Mack Publishing Co., Easton, Pa. (1980)

Homogeneous samples are used for structural and functional characterization using tryptic analysis, amino acid sequencing, antibody production, and assessment of biological activity, such as inhibition of in vitro protein synthesis (ribosome inactivation) and anti-HIV activity.

Genomic and cDNA clones encoding GAP 31, DAP 30 or DAP 32 are cloned based on knowledge of partial amino acid sequences (see Table 1). Oligonucleotide primers designed from these sequences may be used in the polymerase chain reaction (PCR) to specifically amplify the DNA by, for example, one of two methods.

In the first method, two primers encoding two ends of the peptide are used in PCR with poly (A+) mRNA and genomic DNA as template. The genomic or cDNA fragment thus amplified are cloned into the plasmid pUC18, making use of restriction sites added to the 5'-end of the oligonucleotide primers. This method requires very little starting material for use as a template.

In the second method, a single specific primer is used. Lambda phage libraries generated from genomic DNA or cDNA are used as template. Using the PCR reaction to amplify specific clones is more sensitive than directly screening the plated libraries with labelled oligonucleotide. Phage DNA from the libraries is prepared from a plated lysate, and the mixture is used as a template in PCR. One of the primers is designed from the specific amino acid sequence of the peptide, and the other primer is complementary to the lambda phage vector near one end of the cloning site. With appropriate stringency in the PCR conditions, few specific clones should be amplified. In this method, only one specific primer is necessary.

High molecular weight genomic DNA is isolated from the appropriate plant tissue (seeds or leaves). There are several problems unique to isolation of nucleic acids from plant tissues. First, the plant cell wall is difficult to disrupt without shearing high molecular weight DNA. Second, crude plant extracts contain large quantities of polysaccharides, tannins, and pigments which copurify with nucleic acids and interfere with subsequent analysis and enzymatic manipulation.

Freshly harvested Dianthus or gelonium leaves may be quick frozen in dry ice and used immediately for the preparation of genomic DNA or mRNA. The frozen leaves can also be stored at −70° C. until use. For DNA preparation, frozen tissue can be homogenized without damage to high molecular weight DNA using a mortar and pestle in liquid nitrogen. For example, for isolation of genomic DNA, 5 grams of powdered plant tissue are resuspended in a 50 ml extraction buffer consisting of 100 mM Tris HCl pH 8.0, 0.7 M NaCl, 10 mM EDTA, 1% 2-mercaptoethanol, and 1% (w/v) cetyl triammonium bromide (CTAB), and incubated at 55° C. for 30 minutes. The detergent CTAB efficiently disrupts the cell wall and forms a soluble complex with nucleic acids in the presence of the high salt (0.7 M NaCl). The mixture is then cooled to room temperature and extracted twice with chloroform/isoamyl alcohol. The aqueous layer is centrifuged at 4,000×g for 10 minutes, and any precipitate is discarded. The supernatant is then diluted with an equal volume of precipitation buffer, consisting of 100 mM Tris HCl pH 8.0, 10 mM EDTA, 1% CTAB, and allowed to stand at room temperature for 1 hour. As the salt concentration is reduced below 0.4 M NaCl, the CTAB-nucleic acid complex precipitates, leaving the polysaccharides and other contaminants in solution. The mixture is then centrifuged at 4,000×g for 30 minutes.

The pellet is resuspended in 10 mM Tris, 1 mM EDTA (TE), and extracted twice with phenol/chloroform, and once with chloroform/isoamyl alcohol. The solution is made 0.3 M with sodium acetate, and three volumes of ethanol are layered on top. Genomic DNA is spooled from the solution by stirring with a sterile glass rod. The DNA is rinsed with 70% ethanol, dried briefly, and resuspended in TE at 1 mg/ml. By agarose gel electrophoresis, the size of the DNA prepared in this way has been determined to be over 20 kb. In one preparation, for example, the yield from 1 gram of starting material was found to be about 0.2 mg of high molecular weight DNA.

RNA is prepared from these plant tissues by blending the frozen tissue in the presence of liquid nitrogen into powder, and homogenizing the powder in 10 weight volumes of RNAzol, a commercially available extraction agent which contains guanidine isothiocyanate, SDS, and phenol (Cinna/Biotecx, Texas). The homogenate is expected to contain polysaccharides, and is centrifuged at 4,000×g for 30 minutes at 4° C. The supernatant is carefully removed, leaving behind a gelatinous mass. The supernatant is extracted twice with an equal volume of chloroform; DNA and protein form an insoluble complex at the interface. RNA is precipitated from the aqueous layer with isopropanol. The pellet is resuspended, extracted with phenol:chloroform, chloroform/isoamyl alcohol, and precipitated with 3 volumes of ethanol to yield total cellular RNA. Poly (A+) RNA is isolated by chromatography on oligo-dT cellulose. Yields of 2–5% of RNA are routinely obtained.

cDNA and genomic libraries are cloned into lambda gt11 vector using established methods. Use of the EcoR1 site of gt11 offers specific advantages, as it is possible to use one primer complementary to the β-galactosidase gene adjacent to the cloning site to amplify specific clones, using another primer complementary to the specific gene (i.e., the GAP 31, DAP 30 or DAP 32 gene).

cDNA synthesis is performed according to the procedure of Gubler et al. (*Gene* 25:263 (1983)). First strand cDNA is synthesized using poly (A+) RNA as template and using murine Moloney leukemia virus reverse transcriptase with oligo-dT as primer. Second strand cDNA is made using DNA Polymerase I and *E. coli* ligase in the presence of RNAse H. Double-stranded cDNA is made blunt ended with T4 polymerase, and the resulting cDNA was treated with EcoR1 methylase. EcoR1 linkers are then added, and the cDNA is ligated to lambda gt11 arms and packaged into phage.

Genomic DNA is partially digested with MboI and size-selected for fragments of 15–23 kb by preparative agarose gel electrophoresis. These fragments are then made blunt-ended, treated with EcoR1 methylase, and cloned into lambda gt11 with EcoR1 linkers.

Oligonucleotide primers for PCR are designed from the amino acid sequence of GAP 31, DAP 30 or DAP 32. Because the degeneracy of the genetic code increases the number of possible codon choices at each position, in order to account for every possibility, a mixture of oligonucleotide primers is used. One of these primers is exactly complementary to the gene in that region. Alternatively, the primers are made longer, and each possibility is not accounted for. In this latter case, the length of the primer and the first two bases of each codon confer the specificity required. Although the exact complement of the gene is not present, the primer is sufficiently specific for use in the PCR.

The preferred primers have a length of about 14 to about 20 nucleotides, initially, with degeneracy of 1024 or less. A hexanucleotide containing a restriction fragment recognition site, such as HindIII, is added to the 5′-end of the primers for use in cloning.

The following 14-base oligonucleotide primer/probe has been designed based on the N-terminal amino acid sequence unique to GAP 31. This oligonucleotide has a degeneracy of 128:

The following 14-base oligonucleotide primer/probe has been designed based on the N-terminal amino acid sequence unique to DAP 32. This oligonucleotide has a degeneracy of 128:

```
            Residue
     Thr —Lys —Gly —Ala —Thr
 5'  ACA—AAA—GGA—GCA—AC  3'   (SEQ ID NO: 10)
      T        T    T
      G        G    G
      C        C    C 3'  TGT—TTT—CCT—CGT—TG  5'
      A    C    A    A
      C         C    C
      G         G    G
```

The following 14-base oligonucleotide primer/probe has been designed based on the N-terminal amino acid sequence unique to DAP 30. This oligonucleotide has a degeneracy of 128:

```
            Residue
     Ala —Val —Lys —Thr —Ile
 5'  GCA—GTA—AAA—ACA—AT  3'   (SEQ ID NO: 11)
      T    T    G    T
      C    G         G
      G    C         C 3'  CGT—CAT—TTT—TGT—TA  5'
      A    A    C    A
      C    C         C
      G    G         G
```

The following 14-base oligonucleotide primer/probe has been designed based on the N-terminal amino acid sequence unique to DAP 30. This oligonucleotide has a degeneracy of 128:

```
            Residue
     Ala —Thr —Ala —Tyr —Thr
 5'  GCA—ACA—GCA—TAT—AC  3'   (SEQ ID NO: 12)
      T    T    T    C
      G    G    G
      C    C    C 3'  CGT—TGT—CGT—ATA—TG  5'
      A    A    A    G
      C    C    C
      G    G    G
```

The following 24-base oligonucleotides complementary to the β-galactosidase gene near the EcoR1 cloning site have been used as primers in PCR:

(SEQ ID NO: 13)
Lambda 1  5' GGTGGCGACGACTCCTGGAGCCCG 3'

(SEQ ID NO: 14)
Lambda 2  5' TTGACACCAGACCAACTGGTAATG 3'

In conjunction with a single sequence-specific primer, the lambda primers are used to amplify specific clones from genomic and cDNA libraries, as well as to obtain overlapping clones which encode areas outside of known nucleotide sequences. Oligonucleotides are synthesized using an Applied Biosystems 380B synthesizer using the phosphorimidate method, and purified by HPLC. A 5' phosphate group is added using T4 kinase.

Using the two primer approach, both oligonucleotides are designed to encode separate portions of the peptide. The template is either genomic DNA or cDNA. Using the one primer method, the other primer is a lambda primer and the template is a mixture of phage DNA isolated from the libraries.

Reviews of the polymerase chain reaction are provided by Mullis, K. B. (Cold Spring Harbor Symp. Quant. Biol. 51:263-273 (1986)); Saiki, R. K., et al. (Bio/Technology 3:1008-1012 (1985)); and Mullis, K. B., et al. (Met. Enzymol. 155:335-350 (1987)).

PCR reaction condition variables include annealing temperature, polymerization time, and ratio of template to primers. In one embodiment, 100 ng of cDNA or 1 μg of total genomic DNA or mixed phage library DNA is used as template. Then, 5-100 pmol of oligonucleotide primer is used, depending upon the degeneracy of the primer. PCR reactions are carried out in a programmable thermal cycler.

A typical cycle consists of 94° C. denaturation for 1 minute, 45° C. annealing for 2 minutes, and 72° C. polymerization for 3 minutes for the first 20 cycles, followed by an additional 20 cycles during which the polymerization time is incrementally increased by two seconds each cycle. Reaction products are analyzed by agarose gel electrophoresis using conventional agarose for products 500 bp to several kilobases, and NuSieve agarose for products 100 bp to 2 kb.

The genomic or cDNA fragment thus amplified is cloned making use of restriction sites added to the 5'-end of the oligonucleotide primers. The PCR reaction products are digested with restriction enzyme, and cloned into a pUC18 vector which has been linearized at the appropriate site and treated with calf intestinal phosphatase. These clones are then screened using radiolabelled gel-purified DNA corresponding to the major PCR products.

These clones are used to screen genomic and cDNA lambda phage libraries for overlapping clones. In addition, sequence information from these clones is used to design new primers for single-primer PCR amplification from phage libraries. Alternatively, primer extension using sequences derived from these clones is used to generate full length cDNA clones.

Techniques for synthesizing such oligonucleotides are also disclosed by, for example, Wu, R., et al., Prog. Nucl. Acid. Res. Molec. Biol. 21:101-141 (1978)). Procedures for constructing recombinant molecules in accordance with the above- described methods are disclosed by Sambrook, J. T. et al., Molecular Cloning: A Laboratory Manual, Second Ed., Cold Spring Harbor Press, Cold Spring Harbor, N.Y. (1984). These two references are hereby incorporated by reference.

The cloned genes for GAP 31, DAP 30 or DAP 32 can be expressed in prokaryotic expression vectors or in eukaryotic expression vectors, which are known in the art.

An "expression vector" is a vector which (due to the presence of appropriate transcriptional and/or translational control sequences) is capable of expressing a DNA (or cDNA) molecule which has been cloned into the vector and of thereby producing a polypeptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, if a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing the plant protein of the invention in order to produce a prokaryotic genomic expression vector library. Procedures for preparing cDNA and for producing a genomic library are disclosed by Sambrook et al., (supra).

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the gene sequence coding for the protein may be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a sequence encoding the desired protein) are said to be "operably linked" if the nature of the linkage between the two DNA sequences does not (1) result in the introduction of a frame-shift mutation, (2) interfere with the ability of the promoter region sequence to direct the transcription of the gene to be expressed, or (3) interfere with the ability of the gene sequence which is to be expressed to be transcribed by the promoter region sequence. A promoter region would be operably linked to a DNA sequence if the promoter were capable of effecting transcription of that DNA sequence. Thus, to express the protein, transcriptional and translational signals recognized by an appropriate host are necessary.

A promoter is a double-stranded DNA or RNA molecule which is capable of binding RNA polymerase and promoting the transcription of an "operably linked" nucleic acid sequence. As used herein, a "promoter sequence" is the sequence of the promoter which is found on that strand of the DNA or RNA which is transcribed by the RNA polymerase. A "promoter sequence complement" is a nucleic acid molecule whose sequence is the complement of a "promoter sequence." Hence, upon extension of a primer DNA or RNA adjacent to a single-stranded "promoter sequence complement" or, of a "promoter sequence," a double-stranded molecule is created which will contain a functional promoter, if that extension proceeds towards the "promoter sequence" or the "promoter sequence complement." This functional promoter will direct the transcription of a nucleic acid molecule which is operably linked to that strand of the double-stranded molecule which contains the "promoter sequence" (and not that strand of the molecule which contains the "promoter sequence complement").

Certain RNA polymerases exhibit a high specificity for such promoters. The RNA polymerases of the bacteriophages T7, T3, and SP-6 are especially well characterized, and exhibit high promoter specificity. The promoter sequences which are specific for each of these RNA polymerases also direct the polymerase to utilize (i.e. transcribe) only one strand of the two strands of a duplex DNA template. The selection of which strand is transcribed is determined by the orientation of the promoter sequence. This selection determines the direction of transcription since RNA is only polymerized enzymatically by the addition of a nucleotide 5' phosphate to a 3' hydroxyl terminus.

The promoter sequences of the present invention may be either prokaryotic, eukaryotic or viral. Suitable promoters are repressible, or, more preferably, constitutive. Examples of suitable prokaryotic promoters include promoters capable of recognizing the T4 (Malik, S. et al., *J. Biol. Chem.* 263:1174–1181 (1984); Rosenberg, A. H. et al., *Gene* 59:191–200 (1987); Shinedling, S. et al., *J. Molec. Biol.* 195:471–480 (1987); Hu, M. et al., *Gene* 42:21–30 (1986)), T3, Sp6, and T7 (Chamberlin, M. et al., *Nature* 228:227–231 (1970); Bailey, J. N. et al., *Proc. Natl. Acad. Sci.* (U.S.A.) 80:2814–2818 (1983); Davanloo, P. et al., *Proc. Natl. Acad. Sci.* (U.S.A.) 81:2035–2039 (1984)) polymerases; the $P_R$ and $P_L$ promoters of bacteriophage 1 (*The Bacteriophage Lambda*, Hershey, A. D., Ed., Cold Spring Harbor Press, Cold Spring Harbor, N.Y. (1973); *Lambda II*, Hendrix, R. W., Ed., Cold Spring Harbor Press, Cold Spring Harbor, N.Y. (1980)); the trp, recA, heat shock, and lacZ promoters of *E. coli*; the a-amylase (Ulmanen, I., et al., *J. Bacteriol.* 162:176–182 (1985)) and the s-28-specific promoters of *B. subtilis* (Gilman, M. Z., et al., *Gene* 32:11–20 (1984)); the promoters of the bacteriophages of Bacillus (Gryczan, T. J., In: *The Molecular Biology of the Bacilli*, Academic Press, Inc., NY (1982)); *Streptomyces* promoters (Ward, J. M., et al., *Mol. Gen Genet.* 203:468–478 (1986)); the int promoter of bacteriophage lambda; the bla promoter of the $\beta$-lactamase gene of pBR322, and the CAT promoter of the chloramphenicol acetyl transferase gene of pPR325, etc. Prokaryotic promoters are reviewed by Glick, B. R., (*J. Ind. Microbiol.* 1:277–282 (1987)); Cenatiempo, Y. (*Biochimie* 68:505–516 (1986)); Watson, J. D. et al. (In: *Molecular Biology of the Gene*, Fourth Edition, Benjamin Cummins, Menlo Park, Calif. (1987)); and Gottesman, S. (*Ann. Rev. Genet.* 18:415–442 (1984)).

Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature* (London) 290 304–310 (1981)); and the yeast gal4 gene promoter (Johnston, S. A., et al., *Proc. Natl. Acad. Sci.* (USA) 79:6971–6975 (1982); Silver, P. A., et al., *Proc. Natl. Acad. Sci. (USA)* 81:5951–5955 (1984)). All of the above listed references are hereby incorporated by reference.

Production of GAP 31, DAP 30 or DAP 32, or functional derivatives thereof, can be achieved in insect cells, for example, by infecting the insect host with a baculovirus engineered to express the gene of interest by methods known to those of ordinary skill in the art.

Thus, in one embodiment, sequences encoding GAP 31, DAP 30 or DAP 32 may be operably linked to the regulatory regions of the viral polyhedrin protein (Jasny, *Science* 238:1653 (1987)). When infected with the recombinant baculovirus, cultured insect cells, or the live insects themselves, can produce the encoded protein in amounts as great as 20 to 50% of total protein production. When live insects are to be used, caterpillars are presently preferred hosts for large scale protein production according to the invention.

Plant cell expression systems may be particularly useful for expression of the proteins and derivatives of the present invention, in particular if there is a requirement for plant-specific amino acids in the protein sequence that are unavailable in bacterial or animal cell expression systems. Methods for culturing plants cells and for transferring genes into such cells and expressing these genes are well-known in the art. See: *Methods for Plant Molecular Biology*, Academic Press, New York, 1988, which is hereby incorporated by reference. (The following references refer to pages in the above book). Plant cells may be grown as callus-derived cultures (Smith, R. H., pp. 343–353) and prepared as protoplasts (Potrykus, I. et al., pp. 355–383). Methods for fusion and transformation of plant protoplasts are provided by Power, J. B. et al. (pp. 385–401). Gene transfer may be achieved using Ti plasmid vectors (Rogers, S. G. et al., pp. 423–436) or plant virus vectors, such as cauliflower mosaic virus (Brisson, N. et al., pp. 437–446). Alternatively, DNA may be directly transferred into protoplasts, according to methods described by Paszkowski, J. et al. (pp. 447–460).

Expression of the cloned genes encoding the proteins or functional derivatives of this invention permits the large scale production of the active proteins or functional derivatives. New chimeric molecules can then be created with enhanced biological or therapeutic activity, such as anti-HIV activity, and less toxicity to the host cells, using only the parts of the molecule that are active against virus-infected cells or tumor cells. For example, the GAP 31, DAP 30 or DAP 32 protein, or a portion thereof may be coupled to other proteins having inhibitory and cytotoxic properties, including, but not limited to Ricin A chain, Pseudomonas toxin, Diphtheria toxin, and tumor necrosis factor. Toxins conjugated to antibodies or other ligands, are known in the art (see, for example, Olsnes, S. et al., *Immunol. Today* 10:291–295 (1989; Lord, J. et al., *Adv. Biotechnol. Processes* 11:193–211 (1989); Oeltmann, T. N. et al., *FASEB J.* 5:2334–2337 (1991)). Such coupling may be achieved by chemical means or by recombinant DNA techniques wherein DNA encoding GAP 31, DAP 30 or DAP 32 is linked with DNA encoding another toxic protein, a CD4 molecule or fragment, a monoclonal antibody chain or fragment, such as the heavy chain variable region, and the like.

SCRIPs such as GAP 31, DAP 30 or DAP 32 inhibit protein synthesis by hydrolytic cleavage of a glycosidic linkage between the adenine and the ribose at a specific site $A_{4324}$ on the 28S rRNA, leaving the phosphodiester bonds of the RNA backbone intact. This reaction results in a decrease in the stability of the RNA and renders it sensitive to aniline treatment at pH 4.5, with a fragment of about 450 nucleotides being liberated on cleavage. These same results were observed with treatment of either native ribonuclear protein particles, or naked 28S rRNA. This direct interaction of SCRIPs with naked rRNA affects the stability of cellular RNA upon SCRIP treatment.

Additional conjugates of the GAP 31, DAP 30 or DAP 32, or functional derivative thereof, within the scope of the present invention, include conjugates with antibodies specific for HIV antigens, such as gp120 or gp41 and epitopes thereof (Matsushita, S. et al., *AIDS Res. Hum. Retroviruses* 6:193–203 (1990), which is hereby incorporated by reference), conjugates with the CD4 molecule or a soluble CD4 fragment, and conjugates with antibodies specific for tumor antigens. Such conjugates will allow the targeted delivery of the SCRIP to a site of interest, such as a cell expressing an HIV antigen, to achieve even greater specificity and lower nonspecific toxicity.

In other embodiments, GAP 31, DAP 30 or DAP 32, or a functional derivative thereof, can be conjugated to a hormone, and used therapeutically to treat a tumor having a receptor for that hormone, or to specifically eliminate cells which bind that hormone. This targeted elimination of unwanted cells is based on the inhibitory activity of GAP 31, DAP 30 or DAP 32 for protein synthesis, coupled with the specific targeting provided by the hormone for cells bearing appropriate hormone receptors. Thus, for example, prostate cancer, currently treated with analogs of a gonadotrophin releasing hormone (GnRH), can be treated using GAP 31, DAP 30 or DAP 32 conjugated to GnRH. Acromegaly results from overproduction of growth hormone by somatotrophic cells of the anterior pituitary, which are responsive to the hypothalamic releasing hormone, growth hormone releasing hormone (GHRH). Thus, according to the present invention, GAP 31, DAP 30 or DAP 32 conjugated to GHRH can be used to treat acromegaly. Similarly, Cushing's disease results from overproduction of adrenocorticotrophin by corticotrophs of the anterior pituitary which respond to stimulation by corticotrophin releasing hormone (CRH). According to the present invention, GAP 31, DAP 30 or DAP 32 conjugated to CRH can be used to treat Cushing's disease. In general, a hypothalamic releasing hormone conjugated to GAP 31, DAP 30 or DAP 32 is useful for treating a pituitary adenoma having cells with specific receptors for the releasing hormone. (For review of endocrine and neuroendocrine hormones and receptors, see Williams, R. H., ed., *Textbook of Endocrinology*, Sixth Ed., Saunders, Philadelphia, Pa., 1981; Krieger, D. T. et al., eds., *Neuroendocrinology*, Sinauer Associates, Sunderland, MA, 1980; and Norman, A. W. et al., eds., *Hormones*, Academic Press, New York, N.Y., 1987), which references are hereby incorporated by reference).

The present invention also provides a method for recombinant engineering of the cells of an AIDS patient for in situ expression of GAP 31, DAP 30 or DAP 32. A hybrid plasmid containing the DNA encoding GAP 31, DAP 30 or DAP 32, or encoding a fragment thereof, may be inserted into a retroviral vector under the control of the HIV LTR. For a discussion of the methods involved in retroviral vector production and expression, see, for example, Palmer, T. D. et al., *Proc. Nat'l. Acad. Sci. USA* 84:1055–1059 (1987); Wilson, J. M. et al., *Proc. Nat'l. Acad. Sci. USA* 85:3014–3018 (1988); Zwiebel, J. A. et al., *Science* 243:220–222 (1989), which references are hereby incorporated by reference. Transfected cells containing, for example, an integrated HIV-GAP 31 plasmid would express very low levels of GAP 31 constitutively; however, upon transactivation with HIV infection, production of GAP 31 would be efficiently induced. The continuous presence of GAP 31, endogenously supplied, may have therapeutic benefits beyond those achieved by conventional administration of the protein. The same approach would be used with DAP 30 or DAP 32, or a functional derivative thereof.

To treat patients with HIV infection according to the present invention, GAP 31, DAP 30 or DAP 32, or a functional derivative thereof, is administered to a patient in daily doses ranging from about 1 ng to about 50 mg, more preferably in a range of about 1 µg to about 10 mg. It is understood that the dosage of GAP 31, DAP 30 or DAP 32, or functional derivatives thereof, will be dependent upon the age, sex, health, and weight of the recipient, kind of concurrent treatment, if any, frequency of treatment, and the nature of the effect desired. The ranges of effective doses provided herein are not intended to limit the inventors and represent preferred dose ranges. However, the most preferred dosage will be tailored to the individual subject, as is understood and determinable by one of ordinary skill in the art without undue experimentation.

An alternative therapeutic approach within the scope of the present invention involves alternating treatment, administering one of the proteins or functional derivatives of the present invention followed by either another of the SCRIPs of the present invention or a different SCRIP such as MAP 30 or TAP 29. In such an approach, the dosage of the second drug is preferably the same as the dosage of the first drug. Such alternating therapy should be effective in minimizing the immune response of the subject to either protein since the two proteins are immunologically distinct.

Alternatively, a subject with HIV infection or with AIDS is treated with above-described doses of the plant proteins or functional derivatives of the present invention in conjunction with other known therapeutics, including, but not limited to, AZT, 2'-$\beta$-fluoro-ddI, ddA, ddG, ddC, 2'-$\beta$-fluoro-ddC , d4T, AzddU, phosphonylmethoxyethyladenine, or soluble CD4. For a review of therapeutic agents in HIV infection, see: Mitsuya, H. et al., *FASEB J.* 5:2369-2381 (1991), which reference is hereby incorporated by reference). Preferably, the drugs are administered on alternate days in the recommended amounts of each drug.

GAP 31, DAP 30 or DAP 32 is administered in a pharmaceutical composition, either alone or in combination with another agent, in an effective amount to achieve its intended purpose. Determination of the effective amount is well within the skill in the art.

The protein or pharmaceutical compositions of the present invention may be administered by any means that achieve their intended purpose. For example, administration may be by parenteral routes, including subcutaneous, intravenous, intradermal, intramuscular, intraperitoneal, intrathecal, transdermal, or buccal routes. Alternatively, or concurrently, administration may be by the oral or rectal route. The proteins and pharmaceutical compositions can be administered parenterally by bolus injection or by gradual perfusion over time.

In addition to the protein or functional derivative, these pharmaceutical compositions may contain suitable pharmaceutically acceptable carriers comprising excipients and auxiliaries which facilitate processing of the active compounds into preparations which can be used pharmaceutically. Preferably, the preparations, particularly those which can be administered orally and which can be used for the preferred type of administration, such as tablets, dragees, and capsules, and also preparations which can be administered rectally, such as suppositories, as well as suitable solutions for administration by injection or orally, contain from about 0.1 to about 99 percent, preferably from about 25-85 percent, of active compound(s), together with the excipient.

Suitable excipients are, in particular, fillers such as sugars, such as lactose, sucrose, mannitol, or sorbitol; cellulose preparations and/or calcium phosphates, such as tricalcium phosphate or calcium hydrogen phosphate; as well as binders such as starch paste made using, for example, maize starch, wheat starch, rice starch, potato starch, gelatin, gum tragacanth, methyl cellulose, hydroxypropylmethylcellulose, sodium carboxymethyl cellulose, and/or polyvinylpyrrolidone. If desired, disintegrating agents may also be added, such as the above-mentioned starches as well as carboxymethyl starch, cross-linked polyvinyl pyrrolidone, agar, or alginic acid or a salt thereof, such as sodium alginate. Auxiliaries which can be used in the compositions according to the present invention include flow-regulating agents and lubricants such as silica, talc, stearic acid or salts thereof, and/or polyethylene glycol.

Also included within the scope of the present invention is an antibody specific for GAP 31, DAP 30 or DAP 32, or specific for a functional derivative thereof.

The term "antibody" refers both to monoclonal antibodies which are a substantially homogeneous population and to polyclonal antibodies which are heterogeneous populations. Polyclonal antibodies are derived from the sera of animals immunized with an antigen. Monoclonal antibodies (mAbs) to specific antigens may be obtained by methods known to those skilled in the art. See, for example Kohler and Milstein, *Nature* 256:495–497 (1975) and U.S. Pat. No. 4,376,110. Such antibodies may be of any immunoglobulin class including IgG, IgM, IgE, IgA, IgD and any subclass thereof.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316-325 (1983)).

It will be appreciated that Fab and F(ab')$_2$ and other fragments of the antibodies useful in the present invention may be used for the detection and quantitation of the protein of the present invention in the same manner as an intact antibody. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopic determinants usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen.

An antigen may have one, or more than one epitope. The specific reaction referred to above is meant to indicate that the antigen will react, in a highly selective manner, with its corresponding antibody and not with the multitude of other antibodies which may be evoked by other antigens.

The antibodies, or fragments of antibodies, useful in the present invention may be used to quantitatively or qualitatively detect the presence of GAP 31, DAP 30 or DAP 32. For example, it would be of benefit to monitor the level of the protein in the circulation or in the tissues of a subject receiving therapeutic doses of the protein. Thus, the antibodies (of fragments thereof) useful in the present invention may be employed histologically to detect the presence of GAP 31, DAP 30 or DAP 32.

An assay for GAP 31, DAP 30 or DAP 32 typically comprises incubating a biological sample from the subject in the presence of a detectably labeled antibody or antibody fragment capable of identifying the protein and detecting the antibody which is bound in the sample.

Thus, in this aspect of the invention, a biological sample may be treated with nitrocellulose, or other solid support which is capable of immobilizing cells, cell particles or soluble proteins. The support may then be washed with suitable buffers followed by treatment with the detectably labeled specific antibody. The solid phase support may then be washed with the buffer a second time to remove unbound antibody. The amount of bound label on said solid support may then be detected by conventional means.

By "solid phase support" or "carrier" is intended any support capable of binding antigen or antibodies. Well-known supports, or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen or antibody.

The binding activity of an antibody specific for GAP 31, DAP 30 or DAP 32 may be determined according to well known methods, such as enzyme immunoassay (EIA) or radioimmunoassay (RIA). Those skilled in the art will be able to determine operative and optimal assay conditions for each determination by employing routine experimentation.

For EIA, the antibody is detectably labeled by linking to an enzyme. This enzyme, in turn, when later exposed to its substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the antibody or fragments, it is possible to detect binding to the protein of the present invention through the use of a RIA. See, for example: Weintraub, B., *Principles of Radioimmunoassays*, Seventh Training Course on Radioligand Assay Techniques, The Endocrine Society, March, 1986, pp. 1-5, 46-49 and 68-78; Work, T. S. et al., *Laboratory Techniques and Biochemistry in Molecular Biology*, North Holland Publishing Company, NY, 1978. The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The following examples are intended to be illustrative, but not to limit, the invention.

EXAMPLE I

Preparation and Characterization of GAP 31, DAP 30 and DAP 32

The anti-HIV compounds prepared by a three-step procedures consisting of: a) extraction with 10 mM sodium phosphate buffer, pH 7.2, containing 0.15 M NaCl (PBS); b) cationic chromatography of CM 52; and c) affinity chromatography on Con A Sepharose CL 4B.

GAP 31 was purified to homogeneity from the seeds of *Gelonium multiflorum* (*Euphorbiaceae himalaya*). DAP 30 and DAP 32 were purified from leaves *Dianthus caryophyllus* (carnation). The source materials for these preparations were supplied by American Biosciences, New York, N.Y.

The homogeneity and size of the purified anti-HIV agents were determined by SDS-PAGE. Protein sequencing was carried out automated Edman degradation using an Applied Biosystems model 470A protein sequencer, with on-line PTH analyzer.

Shelled *Gelonium multiflorum* seeds or cleaned *Dianthus caryophyllus* leaves were extracted with PBS at ratios of 1:5 or 1:2 (W/V) respectively. Extraction was carried out in a tissue blender for 6 minutes at 4° C. The extract was stirred gently overnight followed by centrifugation at 16,000×g for 30 minutes to remove cell debris. The cleared supernatant was fractionated by ammonium sulfate precipitation to 90% saturation. The precipitate was dissolved in 5mM sodium phosphate, pH 6.4 (buffer A), dialyzed against the same buffer and further purified by column chromatography on CM52. The column was eluted with a linear gradient of 0 to 300 mM NaCl in buffer A (15× column volume). The anti-HIV activity was eluted at about 100 to 260 mM NaCl. GAP 31 was eluted between about 200 and 260 mM NaCl. DAP 30 and DAP 32 were eluted at about 140 and 180 mM NaCl, respectively.

Active fractions were pooled and concentrated by ultrafiltration with Amicon B15 or by ammonium sulfate precipitation to 85% saturation. The samples were then dialyzed against buffer A and further purified using Concanavalin A (Con A)-Sepharose 4B. This step was very effective in the removal of toxic contaminants. Impurities were excluded from the column, whereas the anti-HIV activity was selectively bound to Con A and retained on the column. GAP 31 was eluted from the column with 0.1 M α-methylmannoside in buffer A. DAP 30 and DAP 32 were eluted with 0.25M α-methylmannoside in buffer A or with 60 mM sodium borate in 10 mM Tris-HCl, pH 7.4.

The homogeneity and size of the purified material were determined by SDS-PAGE. Single bands with MW of 31, 30 or 32 kDA were obtained for GAP 31, DAP 30 and DAP 32 respectively (FIG. 1). Identical results were obtained both under reducing and non-reducing conditions, indicating that these molecules are single chain polypeptides.

EXAMPLE II

N-terminal Amino Acid Sequence of GAP 31, DAP 30 and DAP 32

Multiple forms of ribosome-inactivating proteins have been isolated from *Gelonium multiflorum* and *Dianthus caryophyllus* (Stirpe, F. et al., 1980, supra; Stirpe, F. et al., 1981, supra). However, no amino acid sequence data has been reported. Thus no comparison can be made with the sequence of anti-HIV proteins of the present invention. The results reported herein represent the first amino acid sequence information on these three proteins, or, for that matter, on any proteins from these plants.

The N-terminal amino acid sequences of GAP 31 (SEQ ID NO:1), DAP 30 (SEQ ID NO:2) and DAP 32 (SEQ ID NO:3) are shown in Table 1. Comparison of the N-terminal sequence of these proteins with those of TAP 29 (SEQ ID NO:4), MAP 30 (SEQ ID NO:5), saporin-6 (SAP 6) (SEQ ID NO:6), trichosanthin (SEQ ID NO:7) and ricin A chain (SEQ ID NO:8), reveals little homology. When considering identical residues, GAP 31 shows only 0.2, 6.8, and 11% homology to ricin A chain, MAP 30, and trichosanthin respectively. When both identical and conserved residues are considered, GAP 31 shows 22.7% homology to each of the three proteins. Similar, DAP 30 and DAP 32 shows about 8% homology for identical residues and 14% homology for conserved residues with MAP 30, trichosanthin, and ricin A chain. Most homology was found in aromatic (tyrosine and phenylalanine), hydrophobic, and hydroxy-containing amino acids. Furthermore, GAP 31 shows little homology with DAP 30 and DAP 32 (about 7% identical and 12% conserved residues). Although the sequences of the two DAPs differ, 54.5% identity was found in the N-terminal 60 amino acid overlap.

Comparison of the GAP 31, DAP 30 and DAP 32 sequences to the EMBL data bank reveals some interesting findings. As seen Table 1, both DAP 30 and DAP 32 show significant homology to saporin-6, a SCRIP isolated from *Saponaria officinalis* (Benatti, L. et al., *Eur. J. Biochem.* 183:465-470 (1989)). In the N-terminal 60 amino acid overlap, 65% identity was found between DAP 30 and saporin-6. This homology, led the present inventors to assay SAP-6 for antiviral activity and cytotoxicity. As predicted, it exhibited similar levels of anti-HIV activity and cytotoxicity to DAP 30.

EXAMPLE III

DNA Topoisomerase Activity of GAP 31, DAP 32 and DAP 30

Table 2 shows extensive homology between GAP 31 (residues 1-40) and a DNA topoisomerase II, residues 660-699 (SEQ ID NO:9) Wyckoff, E. et al., *J. Mol. Biol.* 205:1-13 (1989)). In a

TABLE 2

Comparison of N-terminal Amino Acid Sequence of GAP 31 with DNA Topoisomerase II

```
                 1                    10                      20
GAP 31       G L D T V S F S T K G A T Y I T Y V N F
             | |           | | |         | | |   : |
DNA TOPO II  G L P E R Y L Y T K G T K S I T Y A D F
             660                                          679

21                   30                      40
GAP 31       L N E L R V K T K P E G N S H G I P S L
             : |       |           |   :       | | | |
DNA TOPO II  I N L E L V L F S N A D N E R S I P S L
             680                                          699
```

Homology of the N-terminal amino acid sequence of GAP 31 with DNA topoisomerase II (DNA-gyrase residues 660 to 699) from drosophila melanogaster ((Wyckoff, E. et al., supra). Sequences were aligned to show maximum similarity. Solid lines indicates identical amino acids. Dots indicate conserved amino acids.

40 amino acid overlap, 40% identity was found. By the conservative identification, a 47.5% homology was found. The identical and conserved residues are aligned perfectly, without requiring any gaps. Further inspection of the sequences shows that a stretch of eight residues, ITYVNFLN of position 15-22 in GAP 31, is homologous to ITYADFIN at position 674-681 of DNA topoisomerase II. The complete homology over an octapeptide may imply a functional similarity between these proteins. The significance of this homology between an anti-HIV protein and a DNA specific endonuclease is intriguing. Although these proteins have distinct specificities, they may share a common mode of action.

Figure 6:
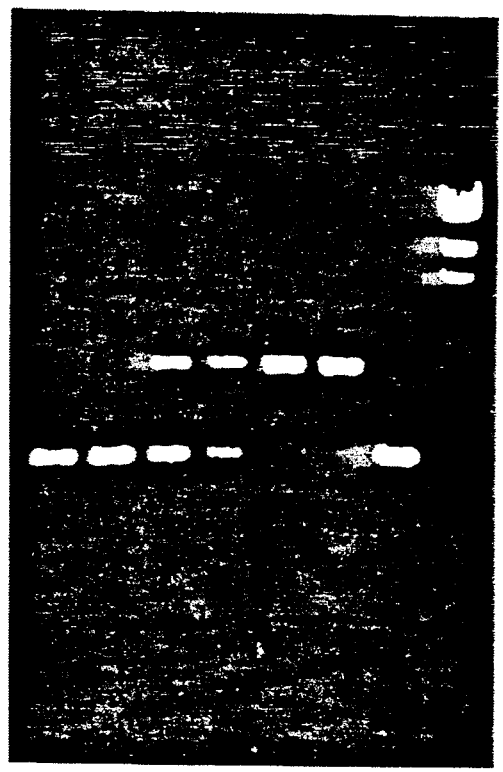
FIG. 6 is a graph showing the DNA topoisomerase activity of GAP 31, DAP 30 and DAP 32 analyzed by electrophoresis in 1% agarose at 50 V. The DNA run in the various lines was treated with following agents: Ta - TAP 29; M - MAP 30; $D_0$ - DAP 30; $D_2$ - DAP 32; Tp - topoisomerase I; G - GAP 31; C- control pCu19 supercoiled DNA; lambda - lambda HindIII partial digest.

The homology between the proteins of the present invention and DNA topoisomerase II led the present inventors to test DNA topoisomerase-like activity in GAP 31 and the other anti-HIV proteins. In this assay, supercoiled plasmid DNA from pCU19 was used as the substrate. The reaction mixture contained (in 10 μl) 400 ng supercoiled DNA, 10 mM Tris-HCl buffer, pH 7.5, 150 mM NaCl, and 1 μg GAP 31 or other protein. The reaction was incubated at 37° C. for 1 hr. The reaction products were analyzed by electrophoresis in 1% agarose in TBE buffer (0.089 M Tris-HCl, 0.089 M boric acid and 0.062 m EDTA) Electrophoresis was carried our at room temperature at 50 V. The gel was stained with ethidium bromide (0.5 μg/ml) for 30 min. and destained in distilled water for 3 hours prior to photodocumentation using a short wavelength UV lamp. The results are shown in FIG. 6.

GAP 31, DAP 32 and DAP 30 exhibited DNA topoisomerase activity by relaxing the supercoiled DNA substrate. In contrast, MAP 30 and TAP 29 lacked such activity under these assay conditions.

DNA topoisomerase I and II are specific markers of cell proliferation (Heck, M. M. S et al., *J. Cell Biol.* 103:2569 (1986)). These enzymes have been the suggested target of several antitumor drugs such as amsacrine and etoposide (Miller, K. G. et al., *J. Biol. Chem.* 259:13560 (1984); Nelson, E. M. et al., *Proc. Natl. Acad. Sci. USA* 81:1361 (1984)). The association of a virus specific topoisomerase I activity with HIV particle and equine infectious anemia virus core has been reported recently (Priel, E. et al., *EMBO J.* 9:4167 (1990)). This enzyme is different from the cellular topoisomerase I enzyme. It is likely that the integration and expression of proviral DNA requires topological conversions of the DNA. The anti-HIV proteins of the present invention may be acting competitively for the viral DNA affecting its integration and expression. If DNA topoisomerase I indeed plays a role in the viral life cycle, it could provide a novel means for intervention in HIV infection.

GAP 31 is an anti-HIV SCRIP capable of hydrolytic cleavage of a glycosidic linkage between the adenine and the ribose at A4324 on the 28S rRNA (Endo, Y. et al., 1987, supra). This function requires that recognition of a specific base sequence in the 28S rRNA. GAP 31 may exert its effects on specific sequences within the HIV-1 viral RNA or its DNA transcript. Topoisomerase II, on the other hand, is a specific endonuclease which causes double-stranded breaks at hypersensitive sites of DNA. This action is essential for the topological conversions required during replication, transcription and chromatin assembly (Holm, C. et al., *Cell* 41:5535-63 (1985)). The precise structure of these recognition sites for the N-glycosidase and topoisomerase II is not known. It is known, however, that these binding sites are commonly conserved and located in the loop regions of the nucleic acids (Moazed, D. et al., *Nature* 334:362-364 (1988)). Consequently, these sites may be the preferred targets for the integration of retrovirus as well (Rohdewohld, H. et al., *J. Virology* 61:336-343 (1987)).

EXAMPLE IV

Other Structure-Function Features of the Anti-HIV Proteins

Recently, the present inventors reported that two related anti-HIV protein from trichosanthes displayed significant difference in cytotoxicity (Lee-Huang et al., 1991, supra). Although their N-amino acid sequences were homologous, a stretch of five residues at position 12-16, KKKVY, in the non-toxic TAP 29 and SSYGV in the toxic trichosanthin differ completely (Gu, Z. et al., supra; Palcca, J. *Science* 247:1406 (1990); McGrath M. S. et al., supra; Collins, E. J. et al., *J. Biol. Chem.* 265:8665-8669 (1990); Chow, T. P. et al., *J. Biol. Chem.* 265:8670-8674 (1990)).

Examination of other nontoxic anti-HIV proteins, such as MAP 30 (Lee-Huang et al., 1990, supra) as well as GAP 31 and DAP 32 as compared with relatively toxic proteins DAP 30, SAP-6 (Stirpe, F. et al., *Biochem. J.* 195:399-405 (1981)) and ricin A chain (Zhang, X. et al., supra), indicated the absence of basic amino acids in all the toxic anti-HIV proteins (see Table 3). Although their amino acid sequences at the N-terminal portion of 44 residues are highly homologous, a stretch of five residues at positions 12-16 show greater variation. For example, the nontoxic TAP 29 sequence is Lys-Lys-Lys-Val-Tyr, which differs completely from the sequence of the toxic trichosanthin, which is Ser-Ser-Tyr-Gly-Val. Interestingly, all of the nontoxic compounds have one or more Lys or Arg residues in this region; GAP 31 has a Lys at position 10, DAP 32 has a Arg at position 16, and MAP 30 has two Lys or Arg residues in this region; GAP has a Lys at position 10, DAP 32 has a Arg at position 16, and MAP 30 has two Lys residues at positions 12 and 16. These Lys and Arg residues offer potential tryptic cleavage sites. These residues are absent in the corresponding regions of the more toxic SCRIPs, DAP 30, SAP-6, trichosanthin and ricin A chain. These results raise the possibility that the absence of basic residues in this unique region may play a role in the cytotoxicity of these anti-HIV proteins.

Especially striking is the extensive sequence homology (6 out of 7 residues) between DAP 30 (NPSASQY) AND SAP-6 (NPTAGQY) and their similar levels of cytotoxicity. These results raise the possibility that the absence of basic residues in this unique region contributes to the cytotoxicity of these protein.

TABLE 3

Comparison of the N-Terminal Sequence of Nontoxic and Toxic Anti-HIV Proteins

| SCRIP | Amino Acid Sequence<br>10 ............................ 16 | Cytotoxicity |
|---|---|---|
| TAP 29 | —Thr—Ser—Lys—Lys—Lys—Val—Tyr— | — |
| MAP 30 | —Thr—Ile—Lys—Thr—Thr—Thr—Lys— | — |
| GAP 31 | —Lys—Gly—Ala—Thr—Tyr—Ile—Thr— | — |
| DAP 32 | —Val—Ser—Pro—Ser—Ala—Asn—Arg— | — |
| DAP 30 | —Asn—Pro—Ser—Ala—Ser—Gln—Tyr— | + |
| SAP 6 | —Asn—Pro—Thr—Ala—Gly—Gln—Tyr— | + |
| RIC A | —Thr—Val—Gln—Ser—Tyr—Thr—Asn— | ++++ |
| TRI | —Ala—Asn—Ser—Lys—Ser—Tyr—Arg— | ++ |

Basic amino acids, Lys and Arg, are bold faced. SAP-6: saporin-6; TRI - trichosanthin; RIC A - ricin A chain.

EXAMPLE V

Anti-HIV Activity of GAP 31, DAP 30 and DAP 32

A. Effects on HIV-1 Infection

The anti-HIV activities of GAP 31, DAP 30, and DAP 32 were determined by microtiter syncytia formation in infectious cell center assay (Nara, P. L. et al., *Nature* 332:469–70 (1988)), viral core protein p24 expression (Nara, P. L. et al., *AIDS Res. Human Retroviruses* 3:283–302 (1987)), and viral-associated RT activity (Hoffman, A. D. et al., *Virology* 147:326–35 (1985)).

The CEM-ss (syncytium sensitive, Leu-3 positive) cell line was used as the indicator cells for the microtiter syncytial-forming assay. The H9 cell line was used for p24 expression and viral-associated RT activity assays in suspension cultures. HIV-1 virus was prepared and stocked as described previously (18). Cell lines were cultured in RPMI-1640 medium containing 100 U/ml of penicillin-streptomycin and 10% heat-inactivated fetal calf serum (culture medium).

Freshly prepared indicator cells in culture medium at $5 \times 10^4$ in 100 μl were treated with 100 μl of SCRIP at various concentrations, for 90 min. At the end of this period, 100 μl of frozen pre-titrated HIV stock from H×B3/H9 cells, corresponding to about 100 syncytial forming units (SFU), were added for 60 min. The supernatant containing SCRIP and virus was then removed and the cells were washed with culture medium. The cells were then plated onto microtiter wells with 200 μl of culture medium containing drug at the same original concentration. The plates were incubated at 37° C. in a humidified incubator at 5% $CO_2$. Focal syncytium formation representing single infectious virion units was scored at day 5 by examination under an inverted microscope.

Figure 2:
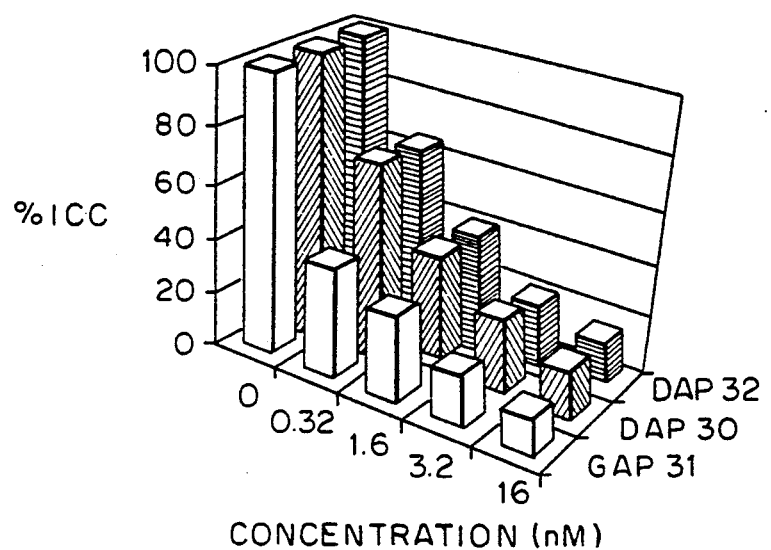
FIG. 2 is a graph showing the effects of GAP 31, DAP 30 and DAP 32 on HIV-1 infection by inhibition of syncytia formation in an infectious cell center assay (ICC). Results represent average values of triplicates from two independent experiments. Triplicate wells of indicator cells containing the test compounds at each concentration without virus were also included for the determination of the cytotoxic and cytostatic activities of these anti-HIV proteins. Infectious cell centers (%ICC) are expressed in terms of Vn/Vo where Vn and Vo are average numbers of syncytia in the drug-treated and untreated samples respectively.

The effects of GAP 31, DAP 30 and DAP 32 on HIV-1 infection were measured by their inhibition of syncytia formation in infectious cell center assays. This assay quantitates acute cell free-HIV infection. It is based on the interaction between fusigenic virus infected cell express the HIV envelop gene products and uninfected adjacent cell bearing CD4 molecules. The results of two independent experiments are summarized in Table 4 and FIG. 2. All of the SCRIPs exhibit dose-dependent inhibition of syncytia formation. $ID_{50}$s of 0.28, 0.83, and 0.76 nM were obtained for GAP 31, DAP 30 and DAP 32 respectively. No cytotoxic or cytostatic effects were observed under the assay conditions. These results suggest that GAP 31, DAP 30 and DAP 32 affect the transmission of HIV-1 gene products through cell contact or release of free virions.

TABLE 4

The Effects of GAP 31, DAP 30 and DAP 32 on HIV Infection Measured by Syncytium Formation in Infectious Cell Center Assay

| Conc nM | Syncytia/well | | | % ICC (Vn/Vo) | | | Cytotoxicity | | |
|---|---|---|---|---|---|---|---|---|---|
| | G31 | D30 | D32 | G31 | D30 | D32 | G31 | D30 | D32 |
| 0 | 77 | 77 | 77 | 100 | 100 | 100 | — | — | — |
| 0.32 | 31 | 32 | 50 | 40 | 68 | 65 | — | — | — |
| 1.6 | 24 | 32 | 31 | 31 | 42 | 40 | — | — | — |
| 3.2 | 15 | 21 | 17 | 19 | 27 | 22 | — | — | — |
| 16 | 10 | 14 | 12 | 13 | 18 | 16 | — | — | — |

Results are means of triplicates from two independent experiments. Triplicate wells of indicator cells containing the testing SCRIPs at each concentration without virus were also included for the determination of the cytotoxic and cytostatic activities of these anti-HIV proteins. Infectious cell center (% ICC) are expressed in terms of Vn/Vo, the ratio of the number of syncytia in the treated and untreated samples.

B. Effects on HIV-1 Replication

Assays of viral core protein p24 expression and HIV-RT activity were carried out in H9 cell cultures. The target cells at log phase were inoculated with viral stock at a multiplicity of infection of $5 \times 10^{-3}$. Cells at $5 \times 10^7$/ml were incubated with the inoculum at 37° C. for 60 minutes to allow viral absorption. Unbound virus was removed by washing with medium. The cells were then resuspended in culture medium and plated at $1 \times 10^5$/ml with or without SCRIP for the duration of the experiment. Under the assay conditions, viral production peaks on day 4. Thus, the cultures were harvested on day 4, and cell-free supernatants of the cultures were collected for the determination of p24 production and HIV-RT activity. The amount of p24 was measured by RIA and expressed in terms of ng/ml. HIV-RT activity was determined by the incorporation of [$^3$H] labeled thymidine with poly(rA).p(dT)$_{12-18}$ as primer-template and expressed in terms of cpm/ml.

Figure 3:
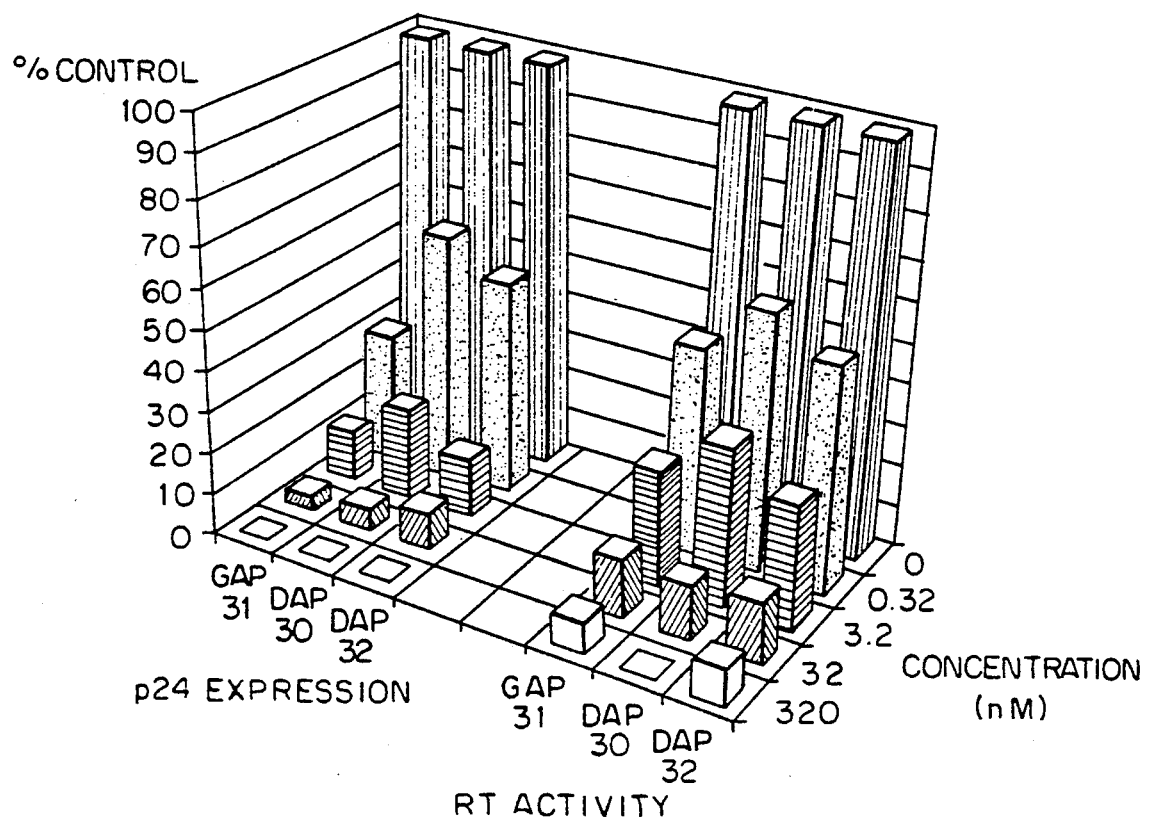
FIG. 3 is a graph showing the effects of GAP 31, DAP 30 and DAP 32 on HIV-1 replication, measured by viral core antigen p24 expression and HIV-RT activity. p24 production was determined by RIA and expressed in ng/ml. Viral-RT activity was determined by the incorporation of [$^3$H]dTTP into TCA-precipitable products and expressed as cpm$\times 10^3$/ml. These values in control culture (without added plant proteins) were 2219 ng/ml and 846$\times 10^3$ cpm/ml, respectively, as determined in triplicates in two independent experiments. Results are normalized to values obtained in control cultures.

The results are shown in Table 5 and in FIG. 3. Each of these compounds demonstrates a dose-dependent inhibition of HIV-1 replication. The $ID_{50}$s for GAP 31, DAP 30 and DAP 32 were 0.23, 0.85 and 0.71 nM for p24 expression, and 0.32, 0.88 and 0.76 nM for HIV-RT activity. The reduction in p24 expression was not due to cytotoxic or cytostatic effects; no inhibition of DNA or protein synthesis was detected at the dose level of the assay. The decrease in HIV-RT activity is likely to be due to an inhibition in virion production, which is also evidenced by the reduced p24 expression.

TABLE 5

The Effect of GAP 31, DAP 32 and DAP 30 on HIV-1 Replication in HIV-infected H9 Cells

| Conc | p24 | | | RT | | | [$^3$H]thymidine | | | [$^3$H]Leucine | | |
|---|---|---|---|---|---|---|---|---|---|---|---|---|
| | G31 | D32 | D30 | G31 | D32 | D30 | G31 | D32 | D30 | G31 | D32 | D30 |
| 0 | 2219 | 2219 | 2219 | 846 | 846 | 846 | 100 | 100 | 100 | 100 | 100 | 100 |
| 0.32 | 688 | 1186 | 1329 | 449 | 468 | 534 | 102 | 100 | 100 | 101 | 99 | 96 |
| 3.20 | 291 | 355 | 515 | 238 | 253 | 329 | 101 | 99 | 97 | 100 | 97 | 89 |
| 32.0 | 67 | 199 | 102 | 119 | 127 | 112 | 100 | 97 | 75 | 99 | 89 | 70 |
| 320 | 0 | 0 | 0 | 59 | 68 | 0 | 100 | 95 | 60 | 96 | 85 | 59 |

Values in this table are averages of triplicates from two independent experiments. Concentration of added anti-HIV proteins are in nM. Values for p24 are in ng/ml. Reverse transcriptase (RT) activity is expressed in cpm/ml ($\times 10^{-3}$). For cellular incorporation of [$^3$H]thymidine or leucine, values represent % of control. Control cpm were 201,000 and 61,000 for thymidine and leucine respectively. G31 = GAP 31; D30 = DAP 30; D32 = DAP 32.

EXAMPLE VI

Cytotoxicity and Toxicity of GAP 31, DAP 30 or DAP 32

The cytotoxicities of the SCRIPs were measured by their effects on cellular DNA and protein syntheses in uninfected H9 cells. Target cells were grown in the absence and presence of various amounts of SCRIPs. The cultures were pulse labeled with 1 µCi of [³H] labeled thymidine or leucine for 8 hours prior to harvesting on day 4. Cellular incorporation of these labeled precursors into trichloroacetic acid (TCA) precipitable products was determined by scintillation counting. Cell viability was determined by trypan blue dye exclusion. Toxicity to intact animals was determined by intraperitoneal injection (i.p.) of the SCRIPs into mice.

Figure 4:
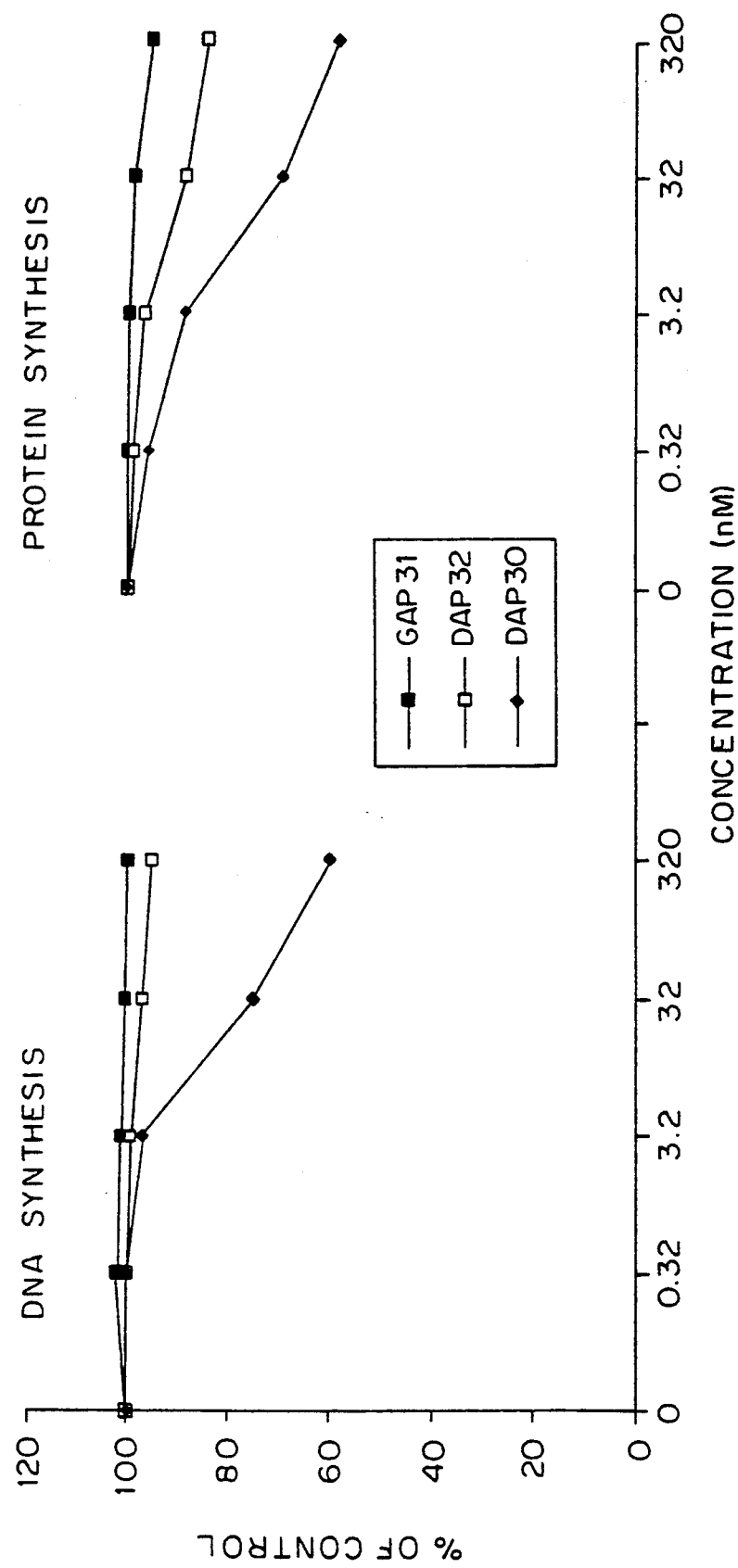
FIG. 4 is a graph showing the cytotoxic activity of GAP 31, DAP 30 and DAP 32, measured as cellular incorporation of [$^3$H] thymidine or leucine into TCA-insoluble material in pulse labeling experiments. H9 cells were seeded at 2$\times 10^4$ cells/well and cultures pulsed with 1 $\mu$Ci (1 Ci=37 GBq) of label 8 hr prior to harvesting at day 4. DNA or protein synthesis were measured by scintillation counting of the incorporation of labelled precursors. Results are normalized to values obtained for controls cultures without added anti-HIV proteins. Control values for thymidine uptake was 201,000 cpm and for leucine was 61,000 cpm. Results are the average triplicate values in two independent experiments.

The results of two independent experiments are summarized in Table 6 and FIG. 4. Experiments were carried out over concentration ranges of 3 orders of magnitude. From 0.32 to 32 nM, GAP 3I and DAP 32 caused no detectable effect on cellular incorporation of labeled thymidine or leucine, while p24 production and HIV-RT activity were inhibited above 90%. At 32 nM however, DAP 30 showed 25 and 30% inhibition of the incorporation of [³H]-labeled thymidine and leucine. At 320 nM, or 1,000×ID$_{50}$, still no inhibition of cellular DNA or protein synthesis was observed for GAP 31. At this concentration, DAP 32 demonstrated 5 and 15% reduction on the incorporation of [³H]-labeled thymidine and leucine respectively and DAP 30 exhibited 40% inhibition of the incorporation of these precursors.

Cytotoxicity to uninfected cells in culture may be expressed as "toxic dose 50" (TD$_{50}$), the dose at which cellular protein and DNA synthesis is inhibited by 50%. The therapeutic index of these SCRIPs, defined as the TD$_{50}$/ID$_{50}$, exceeded 1,000, using any of the three assays of antiviral activity.

The toxicity of these SCRIPs to intact animals was studied on 6–8 weeks old CF$_1$ mice. Filter-sterilized GAP 31, DAP 30 or DAP 32 in PBS was injected i.p. at doses of 0.1, 1.0, 10 and 100 mg per 100 gm body weight every three days. Control animals received similar injection of sterile PBS. The experiments were carried out using four mice each group. Animals were weighted and examined for gross pathological alternations following each injection. The average body weight ranged from 18 to 26 gm. The animals appeared alert and fed normally. Upon the completion of the experiment, the animals were sacrificed and examined. No lesions were observed in any organ, in GAP 31 and DAP 32 treated animals. However mild and moderate hepatic hyperplasia was found in DAP 30 and trichosanthin treated animals respectively. The toxicity results are summarized in Table 6. GAP 31 showed the toxicity to intact mice, with an LD$_{50}$ of 59–64 mg/kg. The LD$_{50}$s for DAP 32 and DAP 30 are 42–46 mg/kg and 12–16 mg/kg respectively. In comparison, the LD$_{50}$s for trichosanthin and ricin are 5–7 mg/kg and 2–3 µg/kg.

EXAMPLE VII

Ribosome-Inactivating Activity of GAP 31, DAP 30 or DAP 32

Ribosome-inactivating activity was measured by cell-free protein biosynthesis in a rabbit reticulocyte lysate system. The reaction was carried out in a total volume of 25 µl containing 2 mM magnesium acetate, 80 mM potassium acetate, 2.5 mM spermidine, 34.5 mg/ml creatine phosphate, 26 mg/ml GTP, 250 mM HEPES buffer, 1 µCi of [3H] leucine and 1 µg of globin mRNA. Incubation was conducted at 37° C. for 30 min. The translation products were resolved by TLC in a solvent system of methanol/water/TCA/glacial acetic acid (30/50/10/10, V/V/W/V). The incorporation of [³H] labeled leucine into TCA precipitable product was measured by scintillation counting.

Figure 5:
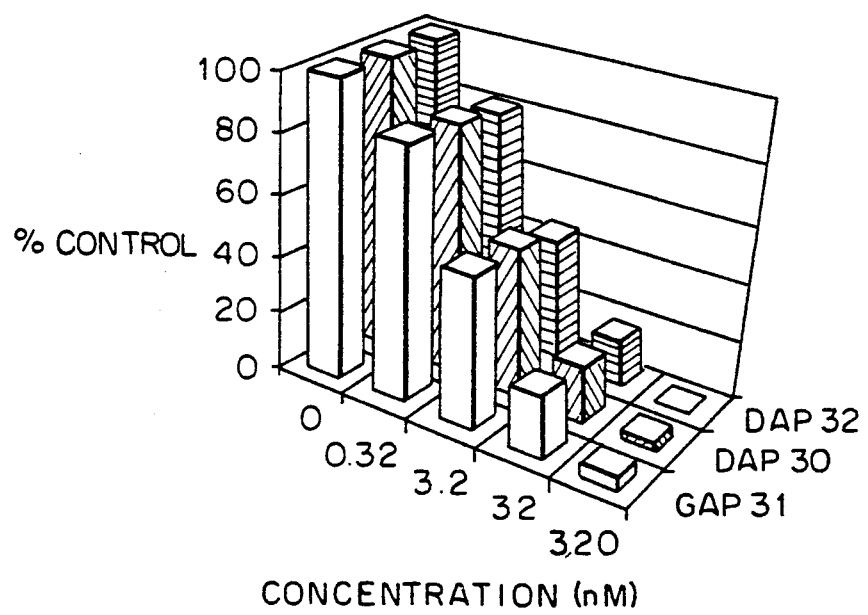
FIG. 5 is a graph showing the ribosome-inactivating activity of GAP 31, DAP 31 and DAP 32, measured as in vitro translation of globin mRNA in a rabbit reticulocyte system. Inhibition of protein synthesis was determined by measuring incorporation of [$^3$H]leucine into TCA-insoluble material as a function of drug concentration. Results are from two independent experiments each run in duplicate. Average control values for leucine incorporation without added anti-HIV protein is 65,000 cpm/$\mu$l. Results are shown as % of control plotted against concentration of the added anti-HIV protein.

The results are shown in Table 6 and FIG. 5. Dose-dependent inhibition of [³H] leucine incorporation was observed in all cases. ID$_{50}$s of 4.1, 3.2 and 2.3 nM were obtained for GAP 31, DAP 30 and DAP 32 respectively. These values are about 14, 4, and 3 times higher than those observed for the anti-HIV activity of these proteins respectively.

TABLE 6

Comparison of Ribosome-Inactivating Activity (A), Anti-HIV Activity (B,C,D), Cytotoxicity (E) and Toxicity (F) of Anti-HIV Proteins

| Protein | ACTIVITY | | | | | |
|---|---|---|---|---|---|---|
| | A | B | C | D | E | F |
| DAP 30 | 3.4 | 0.76 | 0.86 | 0.88 | 910 | 12–16 |
| DAP 32 | 2.3 | 0.76 | 0.31 | 0.36 | >3200 | 42–46 |
| GAP 31 | 4.1 | 0.28 | 0.23 | 0.32 | >3200 | 59–64 |
| MAF 30 | 3.3 | 0.22 | 0.22 | 0.33 | >3200 | 56–62 |
| TAP 29 | 3.7 | 0.34 | 0.37 | 0.42 | >1000 | 37–44 |
| Tri | 3.7 | 0.34 | 0.37 | 0.46 | 340 | 5–7 |
| Ric A | | | | | | 0.002–0.003 |

A: Ribosome-inactivation, ID$_{50}$ in nM
B: Inhibition of syncytium formation, ID$_{50}$ in nM
C: Inhibition of p24 activity, ID$_{50}$ in nM
D: Inhibition of Reverse Transcriptase, ID50 in nM
E: Cytotoxicity, ID$_{50}$ in nM
F: In Vivo Toxicity, LD$_{50}$ in mg/kg (range)

EXAMPLE VIII

MOLECULAR CLONING OF GAP 31, DAP 30 AND DAP 32

Poly A+ mRNA is prepared from *Gelonium multiflorum* (Euphorbiaceae himalaya) or *Dianthus caryophyllus* as-described above. Genomic and cDNA libraries are constructed in lambda gt11 as described above. The library is screened by plaque hybridization using oligonucleotide probes derived from the N-terminal amino acid sequence of TAP 29.

Clones are obtained and sequenced according to standard methods (see above) to determine the nucleotide sequence of the GAP 31, DAP 30 or DAP 32 gene, and, from this, the amino acid sequence of the entire GAP 31, DAP 30 or DAP 32 protein. The cloned gene is expressed in bacterial and eukaryotic cells according to methods described above.

EXAMPLE IX

CONJUGATION OF GAP 31, DAP 30 OR DAP 32 TO ANTI-HIV ANTIBODIES

GAP 31, DAP 30 or DAP 32 is cross-linked to human anti-gp41 or human anti-gp120 monoclonal antibodies using the heterobifunctional reagent, SPDP (N-succinimidyl 3-(2-pyridyldithio)propionate). Purified antibody in phosphate buffered saline is treated with SPDP in 10–15 -fold molar excess for 30 min. at room temperature so as to introduce 2-pyridyl disulfide groups into the IgG molecule. The free SPDP is removed by dialysis. The sample is then mixed with TAP 29 (3-fold molar excess) at 4° C. for 16 hours. The conjugate is separated from unbound TAP 29 by gel filtration on a Sephacryl S-200 column.

The cytotoxic effect of the conjugate is tested on CEM-ss and H9 cells, as described above. The conjugate is shown to have specific cytotoxic activity for HIV infected, but not for uninfected target cells.

The conjugate is used to treat a subject with and HIV infection or AIDS by administration as described above.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

---

What is claimed is:

1. An isolated GAP 31 protein, comprising a 31KDa-protein, as determined on SDS-PAGE, wherein said GAP 31 protein is
   (a) obtainable from the seeds of the plant *Gelonium multiflorum, Euphorbiaceae himalaya;*
   (b) has anti-HIV activity in vitro at concentrations of about 0.3 nanomolar;
   (c) lacks non-specific cytotoxicity in vitro at concentrations of about 300 nanomolar; and
   (d) comprises the amino acid sequence of SEO ID NO:1.

2. An antibody having a binding domain which binds an epitope specific for a GAP31 protein according to claim 1.

3. A pharmaceutical composition comprising a GAP31 protein of claim 1 and a suitable excipient.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 55 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: GAP 31

( x i ) SEQUENCE DESCRIPTION: SEQ ID NO:1:

```
Gly Leu Asp Thr Val Ser Phe Ser Thr Lys Gly Ala Thr Tyr Ile Thr
         5                  10                  15
Tyr Val Asn Phe Leu Asn Glu Leu Arg Val Lys Thr Lys Pro Glu Gly
             20                  25                  30
Asn Ser His Gly Ile Pro Ser Leu Arg Lys Ser Ser Asp Asp Pro Gly
         35                  40                  45
Ser Ser Phe Val Val Ala Gly
     50                  55
```

( 2 ) INFORMATION FOR SEQ ID NO:2:

( i ) SEQUENCE CHARACTERISTICS:
        ( A ) LENGTH: 59 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: DAP 30

( x i ) SEQUENCE DESCRIPTION: SEQ ID NO:2:

```
Ala Thr Ala Lys Thr Leu Asn Leu Ala Asn Pro Ser Ala Ser Gln Tyr
         5                  10                  15
Ser Xaa Phe Leu Asp Gln Ile Arg Asn Asn Val Arg Asp Thr Ser Leu
             20                  25                  30
Ile Tyr Gly Gly Thr Asp Val Ala Val Ile Gly Ala Pro Ser Thr Thr
         35                  40                  45
Asp Lys Phe Leu Arg Leu Asn Phe Gln Gly Pro
     50                  55
```

( 2 ) INFORMATION FOR SEQ ID NO:3:

( i ) SEQUENCE CHARACTERISTICS:
        ( A ) LENGTH: 59 amino acids
        ( B ) TYPE: amino acid
        ( C ) STRANDEDNESS: single
        ( D ) TOPOLOGY: linear ( i i ) MOLECULE TYPE: protein ( i x ) FEATURE:
   ( A ) NAME/KEY: DAP 32

( x i ) SEQUENCE DESCRIPTION: SEQ ID NO:3:

Ala Val Xaa Thr Ile Thr Leu Asn Leu Val Ser Pro Ser Ala Asn Arg
            5               10              15

Tyr Ala Thr Phe Leu Thr Glu Ile Arg Asp Asn Val Arg Xaa Arg Ser
            20              25              30

Leu Asp Tyr Ser His Ser Gly Ile Asp Val Ile Gly Ala Pro Ser Ser
            35              40              45

Arg Ser Xaa Leu Asn Ile Asn Phe Gln Ser Pro
     50              55

( 2 ) INFORMATION FOR SEQ ID NO:4:

( i ) SEQUENCE CHARACTERISTICS:
      ( A ) LENGTH: 45 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: TAP 29

( x i ) SEQUENCE DESCRIPTION: SEQ ID NO:4:

Asp Val Ser Phe Arg Leu Ser Gly Ala Thr Ser Lys Lys Lys Val Tyr
            5               10              15

Phe Ile Ser Asn Leu Arg Lys Ala Leu Pro Asn Glu Lys Lys Leu Tyr
            20              25              30

Asp Ile Pro Leu Val Arg Ser Ser Xaa Ser Gly Ser Lys
            35              40              45

( 2 ) INFORMATION FOR SEQ ID NO:5:

( i ) SEQUENCE CHARACTERISTICS:
      ( A ) LENGTH: 44 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: MAP 30

( x i ) SEQUENCE DESCRIPTION: SEQ ID NO:5:

Asp Val Asn Phe Asp Leu Ser Thr Ala Thr Ala Lys Thr Tyr Thr Lys    1
            5               10              15

Phe Ile Glu Asp Phe Arg Ala Thr Leu Pro Phe Ser His Lys Val Tyr
            20              25              30

Asp Ile Pro Leu Leu Tyr Ser Thr Ile Ser Asp Pro
            35              40      44

( 2 ) INFORMATION FOR SEQ ID NO:6:

( i ) SEQUENCE CHARACTERISTICS:
      ( A ) LENGTH: 60 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: saporin-6 (SAP 6)
      ( B ) LOCATION: 24-83

( x i ) SEQUENCE DESCRIPTION: SEQ ID NO:6:

Arg Val Thr Ser Leu Thr Leu Asp Leu Val Asn Pro Thr Ala Gly Gln
         5                   10                  15

Tyr Ser Ser Phe Val Asp Lys Phe Val Asp Lys Ile Arg Asn Pro Asn
            20                  25                  30

Leu Lys Tyr Gly Gly Thr Asp Ile Ala Val Ile Gly Xaa Pro Pro Ser
        35                  40                  45

Lys Gly Lys Phe Leu Arg Ile Asn Phe Gln Ser Ser
    50                  55              60

( 2 ) INFORMATION FOR SEQ ID NO:7:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Trichosanthin ( x i ) SEQUENCE DESCRIPTION: SEQ ID NO:7:

Asp Val Ser Phe Arg Leu Ser Gly Ala Thr Ser Ser Ser Tyr Gly Val
             5                  10                  15

Phe Ile Ser Asn Leu Arg Lys Ala Leu Pro Asn Glu Arg Lys Leu Tyr
            20                  25                  30

Asp Leu Pro Leu Ile Arg Ser Ser Leu Pro Gly Ser
        35                  40              44

( 2 ) INFORMATION FOR SEQ ID NO:8:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Ricin A chain ( x i ) SEQUENCE DESCRIPTION: SEQ ID NO:8:

Ile Ile Asn Phe Thr Thr Ala Gly Ala Thr Val Gln Ser Tyr Thr Asn
             5                  10                  15

Phe Ile Arg Ala Val Arg Gly Arg Leu Thr Thr Gly Ala Asp Val Arg
            20                  25                  30

His Glu Ile Pro Val Arg Leu Pro Leu Pro Ile Asn
        35                  40              44

( 2 ) INFORMATION FOR SEQ ID NO:9:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: DNA topoisomerase II
        ( B ) LOCATION: 660-699

( x i ) SEQUENCE DESCRIPTION: SEQ ID NO:9:

Gly Leu Pro Glu Arg Tyr Leu Tyr Thr Lys Gly Thr Lys Ser Ile Thr

```
                       5                       10                      15
Tyr Ala Asp Phe Ile Asn Leu Glu Leu Val Leu Phe Ser Asn Ala Asp
                20                      25                  30

Asn Glu Arg Ser Ile Pro Ser Leu
            35              40
```

( 2 ) INFORMATION FOR SEQ ID NO:10:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:10:

ACNAARGGNG CNAC                                                               14

( 2 ) INFORMATION FOR SEQ ID NO:11:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:11:

GCNGTNAARA CNAT                                                              14

( 2 ) INFORMATION FOR SEQ ID NO:12:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:12:

GCNACNGCNT AYAC                                                             14

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

GGTGGCGACG ACTCCTGGAG CCCG                                           24

( 2 ) INFORMATION FOR SEQ ID NO:14:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

TTGACACCAG ACCAACTGGT AATG                                           24